United States Patent [19]

Wolf et al.

[11] Patent Number: 5,256,886
[45] Date of Patent: Oct. 26, 1993

[54] APPARATUS FOR OPTICALLY DETECTING CONTAMINATION IN PARTICLES OF LOW OPTICAL-LOSS MATERIAL

[75] Inventors: William E. Wolf, Chesapeake, Md.; Robert H. Livermore, Horten, Norway; David D. Dreyfuss, Kettering, Ohio; John J. Majeski, Aston, Pa.; Eugene F. Palecki, Wilmington, Del.; Thomas W. Simpson, Boothwyn, Pa.

[73] Assignee: E. I. Du Pont de Nemours and Company, Wilmington, Del.

[21] Appl. No.: 863,961

[22] Filed: Apr. 10, 1992

Related U.S. Application Data

[63] Continuation-in-part of Ser. No. 693,523, Apr. 30, 1991, abandoned, and a continuation-in-part of Ser. No. 693,524, Apr. 30, 1991, abandoned.

[51] Int. Cl.$^5$ ............................................. G01N 15/06
[52] U.S. Cl. ..................................... 250/574; 250/228; 356/338
[58] Field of Search ...................... 250/228, 234–236, 250/563, 573, 574; 356/237, 335, 338, 341, 343

[56] References Cited

U.S. PATENT DOCUMENTS

| | | | |
|---|---|---|---|
| 3,549,263 | 12/1970 | Osawa et al. | 356/209 |
| 3,920,336 | 11/1975 | Sackett | 356/201 |
| 4,186,838 | 2/1980 | Levitt et al. | 209/581 |
| 4,422,760 | 12/1983 | Webster | 356/244 |
| 4,601,576 | 7/1986 | Galbraith | 250/572 |
| 4,626,101 | 12/1986 | Ogawa et al. | 250/563 |
| 4,740,708 | 4/1988 | Batchelder | 250/572 |
| 4,781,742 | 11/1988 | Hill et al. | 65/29 |
| 4,885,473 | 12/1989 | Shofner et al. | 250/574 |
| 4,892,409 | 1/1990 | Smith | 356/414 |
| 4,902,131 | 2/1990 | Yamazaki et al. | 356/336 |
| 4,965,454 | 10/1990 | Yamauchi et al. | 250/372 |
| 4,972,258 | 11/1990 | Wolf et al. | 358/93 |
| 4,976,540 | 12/1990 | Kitamura et al. | 356/38 |

FOREIGN PATENT DOCUMENTS

| | | |
|---|---|---|
| 0373796 | 6/1990 | European Pat. Off. |
| 90058453 | 9/1990 | Fed. Rep. of Germany |
| 2632723 | 6/1988 | France |
| 58-77637 | 7/1983 | Japan |
| 128543 | 5/1989 | Japan |
| 8909392 | 10/1989 | World Int. Prop. O. |

OTHER PUBLICATIONS

Goodman, Joseph W. et al., "Laser Applications", vol. 4 Academic Press, New York (1980), pp. 171–174.
Reynolds Metal Company, "Contamination Detector for Extrudable Dielectrics", Prepared for Electric Power Research Institute, (Final Rpt Jul. 1979).

*Primary Examiner*—David C. Nelms
*Assistant Examiner*—S. Allen

[57] ABSTRACT

An apparatus for optically detecting light-absorbing contamination in at least one particle of low optical-loss material comprises an optical integrating chamber for containing the particles. A laser for emitting a laser beam to illuminate the particles is mounted in the plane of rotation of a rotating mirror such that the laser beam scans in a fan scan. A scanning assembly is mounted in optical alignment with the laser for reflecting the laser beam and for causing the laser beam to scan the particles in the optical integrating chamber. A focusing assembly is mounted in optical alignment with the laser for focusing the scanning laser beam onto the particles in the chamber, the focusing assembly operating in conjunction with the scanning assembly so that light from the laser beam is reflected from the particles and is repeatedly scattered onto the interior walls of the integrating chamber. A light sensing assembly is mounted on the integrating chamber for receiving the repeatedly scattered light from the interior walls of the integrating chamber and for generating a signal indicative of the intensity of the repeatedly scattered light. A decrease in the intensity of the repeatedly scattered light is a function of the presence of light-absorbing contamination in the material.

37 Claims, 21 Drawing Sheets

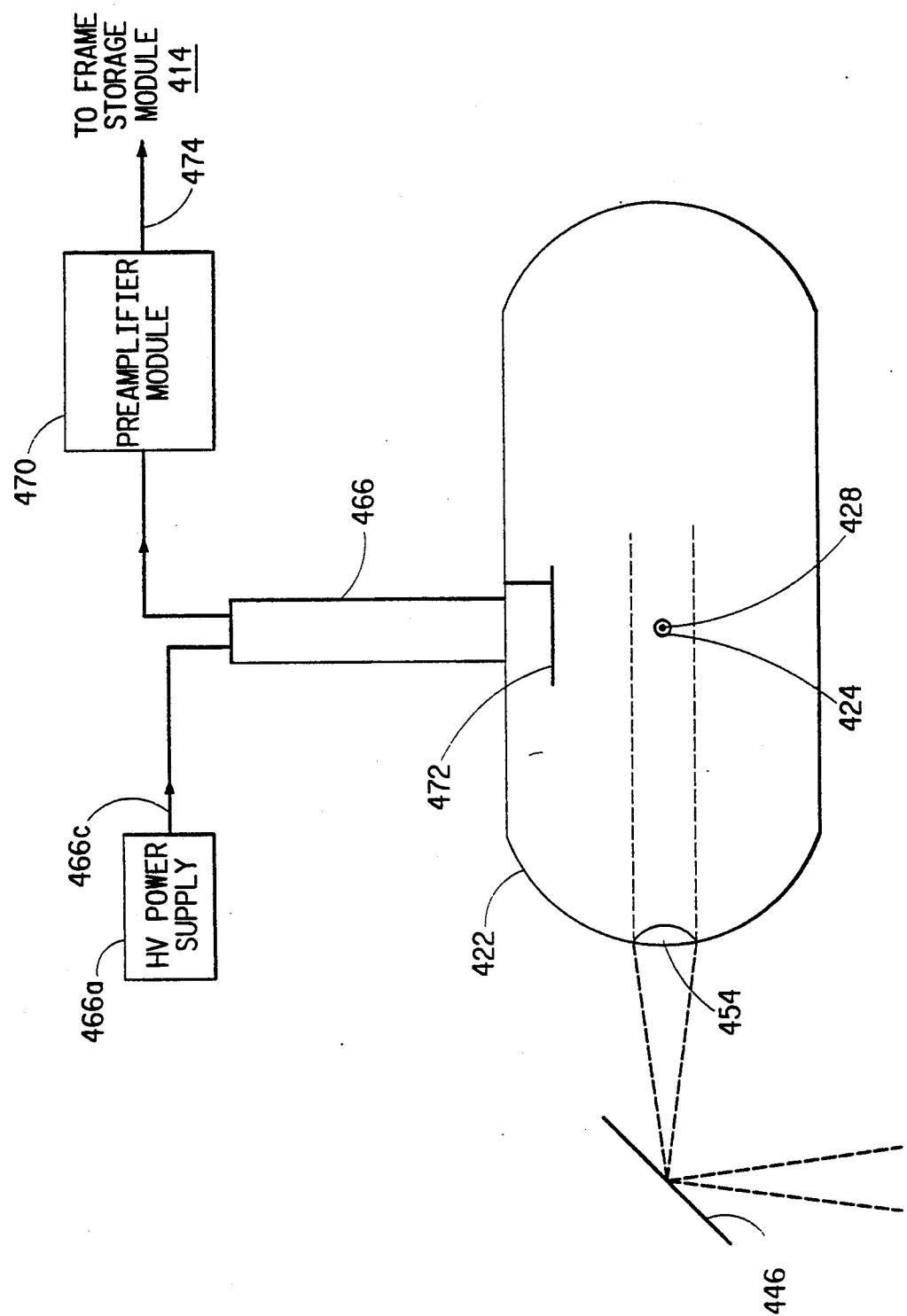

APPARATUS FOR OPTICALLY DETECTING CONTAMINATION IN PARTICLES OF LOW OPTICAL-LOSS MATERIAL

This application is a continuation-in-part of application Ser. No. 07/693,523, filed Apr. 30, 1991, and application Ser. No. 07/693,524, filed Apr. 30, 1991, both now abandoned.

BACKGROUND OF THE INVENTION

1. Field of the Invention

The present invention relates to an apparatus for optically detecting light-absorbing contamination in particles of low optical-loss material, such as polymer powder, beads, or pellets.

2. Description of the Related Art

Engineering materials, such as polymers, ceramics and filler materials used in manufacturing, are sold in particulate intermediate form as pellets before processing into final products. Also, many food products for human and animal consumption are produced in particulate form, pellets, grains and small vegetables being common examples. Medical products such as aspirin tablets, powders and similar materials are also manufactured in intermediate particulate form.

During manufacture and handling of materials in particulate or pellet form, it is possible for various types of contaminants to become mixed in with the material. These contaminants can be in the form of a pellet themselves or mixed in the desirable pellets. In either case, the result is the same—a degradation of the finished product. Ensuring that such particulate materials, in their intermediate form, are free of contaminants is an important quality control consideration.

The problem described above is so widespread in industrial production that many attempts have been made to automate the inspection of particulate material, with varying degrees of success. A number of factors must be considered when developing a system which can inspect particulate material for contamination, including materials handling considerations and the interaction between product handling and optical detection of contamination.

One approach to overcoming the problem described above has been to use a source of illumination, such as an arc lamp of suitable spectral content, and a detector, such as a photomultiplier tube or a PIN diode detector, with the necessary electronic circuitry to detect changes in light flux reflected from or transmitted through the particulate material. The particulate material is passed through the zone of illumination. A measurement in the form of an electrical signal proportional to the light flux provides the information to make a quality judgment. The contaminated particulate material is thus detected. The contaminant occupies a small percentage of the field of view of the detector and causes a relatively small percentage change in light flux. This approach forces the system designer to deal with signals that have a relatively low signal-to-noise ratio. The low signal-to-noise ratio problem usually causes an increase in system complexity and cost and adversely effects the performance of the system. In addition to signal-to-noise problems, the light intensity required in this system to obtain a sufficient contaminant signal amplitude may result in damage to the product due to heating or other light-induced change.

Another approach to optically detecting contamination in particulate material has been to use an illumination concept which is similar to that used in the above-described system with an array of detectors, such as a linear or a two-dimensional charge-coupled device (CCD) array. This approach images small areas of the field of view onto individual photosites and improves the signal-to-noise ratio. However, this approach is subject to signal degradation due to light scattering in the zone of illumination, flare in the imaging optics and crosstalk between photosites in the detector array itself. In addition, this technique is sensitive to the shape and orientation of the particles which may cause specular reflections. These specular reflections can cause large changes in signal level which are not related to the presence of contamination. Complexities result from data handling and analysis, due to timing and data format requirements of the detectors, which result in increased complexity and cost for this type of optical detection system.

It has been observed that under ordinary lighting conditions, a low optical-loss material such as a transparent object can be readily seen because of light intensity variations due to the direction of the illuminating light. It has been shown however, that such low optical-loss materials become nearly invisible when viewed in a perfectly uniform illumination field (see R. W. Wood, *Physical Optics*, third ed., The Macmillan Company, New York, (1934), p. 98). A lossless or transparent object may be placed within an optical integrating chamber and illuminated with light which is of equal intensity in all directions. If a person were to observe the object through a small opening in the integrating chamber, the object would be nearly invisible.

SUMMARY OF THE INVENTION

The foregoing problems associated with detecting contamination in low optical-loss material are overcome by an apparatus designed in accordance with the present invention which takes advantage of the observed optical properties of low optical-loss material. The present invention utilizes an optical integrating chamber in combination with a scanning laser beam which illuminates only a small area of low optical-loss material at any instant in time to detect the presence of light-absorbing contamination.

The present invention takes advantage of the fact that many polymeric materials exhibit low optical-loss characteristics at certain wavelengths, i.e., little of the light incident on the surface of the polymeric material is absorbed. Most of the light incident on the surface of the polymeric material is either reflected by or transmitted through the material. When scanned with a small spot of light, the polymeric material becomes invisible. If the material contains an optically absorbing contaminant, the contaminant becomes visible as a dark spot in a uniform background, and detection of the contaminant is thus enhanced.

It has been found that if a photodetector is arranged within the wall of an integrating chamber to detect the light reflected by or transmitted through a low optical loss object, the light level detected will be unaffected, even if the object is removed from the chamber. Such an arrangement will produce a detected light level which depends solely on the total amount of light reflected or transmitted from the object and not upon the direction of the light. This observed phenomenon forms the basis for the present invention.

Accordingly, it is an object of the present invention to provide an apparatus for detecting light-absorbing contamination in particles of low optical-loss material where the contamination is placed in an integrating chamber and absorbs light, and where a decrease in the intensity of the light repeatedly scattered from the interior walls of the integrating chamber is a function of light-absorbing contamination in the material.

It is further an object of the present invention to provide an apparatus which transports low optical-loss material through an integrating chamber in which the surface characteristics and the surface orientation of the particles are not known.

To achieve the foregoing objects, and in accordance with the purposes of the invention as embodied and broadly described herein, there is provided an apparatus for optically detecting light-absorbing contamination in at least one particle of low optical-loss material. The apparatus comprises an optical integrating chamber for containing the particle. The integrating chamber has interior walls. The apparatus also comprises a laser for emitting a laser beam to illuminate the particle and a scanning assembly mounted in optical alignment with the laser for reflecting the laser beam and for causing the laser beam to scan the particle in the optical integrating chamber. The apparatus also comprises a focusing assembly mounted in optical alignment with the laser for focusing the scanning laser beam onto the particle in the chamber. The focusing assembly operates in conjunction with the scanning assembly so that light from the laser beam is reflected from the particle and is repeatedly scattered onto the interior walls of the integrating chamber. The apparatus also comprises a light sensing assembly for generating an intensity signal indicative of the intensity of the repeatedly scattered light, wherein a decrease in the intensity of the repeatedly scattered light is a function of the presence of light-absorbing contamination in the particulate material.

The present invention results in minimal variations in light level at the light sensing assembly, unless a light-absorbing contaminant is illuminated by the scanning laser beam, in which case the intensity of the light level at the light sensing assembly decreases. With the present invention, particles of acceptable quality become invisible to the light sensing assembly. All the light entering the chamber is directed and focused sequentially to each point being scanned. The focused laser beam is much smaller than a single particle being scanned, resulting in high sensitivity to variations in the optical absorbance of the particulate material. Since the variation of the detected light level for contaminant-free particles is quite small, a signal-to-noise ratio improvement over that of the prior art can be achieved.

The apparatus of the present invention has been found to be well-suited for analyzing materials such as glass cullet, flakes of polyester terephalate, beads of polytetrafluoroethylene, sold by E. I. du Pont de Nemours and Company (hereinafter referred to as Du Pont) under the trademark "TEFLON", crumbs or pellets of hydrocarbon rubber, sold by Du Pont under the trademark "NORDEL", pellets of ionomer resin, sold by Du Pont under the trademark "SURLYN", pellets of nylon molding and extrusion resin, sold by Du Pont under the trademark "ZYTEL", and pellets of acetyl resin, sold by Du Pont under the trademark "DELRIN".

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

BRIEF DESCRIPTION OF THE DRAWINGS

The accompanying drawings, which are incorporated in and constitute a part of the specification, illustrate the presently preferred embodiments of the invention and, together with the general description given above and the detailed description of the preferred embodiments given below, serve to explain the principles of the invention.

FIG. 20 is a partial, cross-sectional, schematic view of the apparatus of FIG. 19 taken along lines 20—20 of FIG. 19 showing the interior of the integrating chamber.

DETAILED DESCRIPTION OF THE PREFERRED EMBODIMENTS

Reference will now be made in details to the preferred embodiments of the invention, examples of which are illustrated in the accompanying drawings. Wherever possible, the same reference numbers will be used throughout the drawings to refer to the same or like parts.

Figure 1:
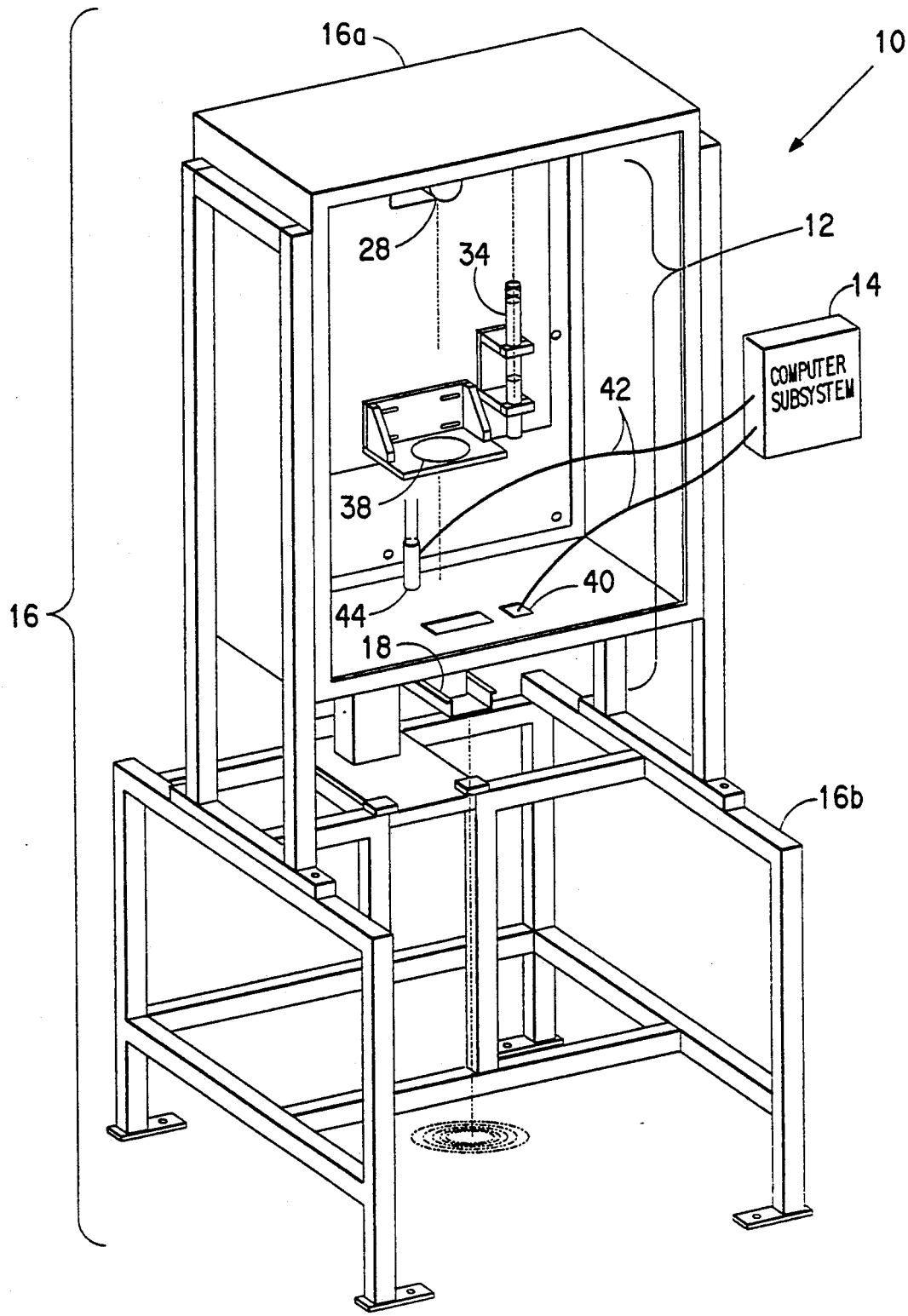
FIG. 1 is an isometric view of the apparatus for optically detecting contamination in particles of low optical-loss material according to a first embodiment of the present invention.

In accordance with a first embodiment of the present invention, there is provided an apparatus for optically detecting light-absorbing contamination in at least one particle of low optical-loss material. A first embodiment of the present invention is illustrated with reference to FIGS. 1-10. Referring to FIG. 1, there is shown generally at 10 an apparatus for optically detecting light-absorbing contamination in particles of optical low-loss material. Apparatus 10 comprises an optical subsystem, shown generally at 12, and a computer subsystem, shown generally at 14. Computer subsystem 14 is connected to optical subsystem 12 as shown in FIG. 1. Optical subsystem 12 is mounted in a suitable support framework 16. Support framework 16 comprises an enclosure 16a for enclosing most of the components of optical subsystem 12 and a stand 16b for supporting enclosure 16a. Support framework 16 is sufficiently rigid to support all of the components of the optical subsystem, to keep them in precise orientation and alignment and to isolate vibrations from the optical subsystem.

Figure 2:
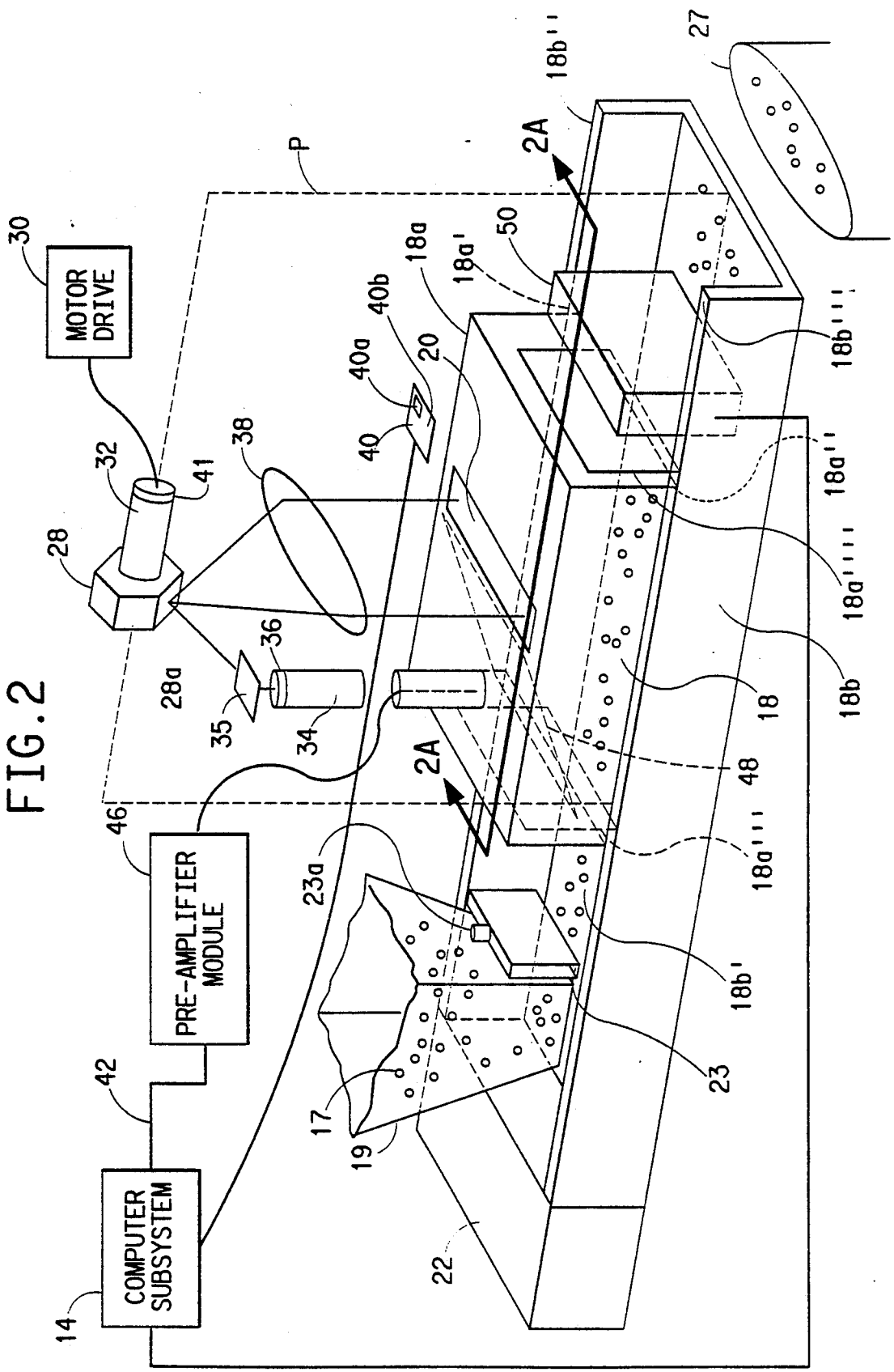
FIG. 2 is a schematic view of the major components of the optical subsystem of the first embodiment of the present invention.

The apparatus for optically detecting light-absorbing contamination of the first embodiment comprises an optical integrating chamber for containing the at least one particle, the optical integrating chamber having a plurality of interior walls. As shown in FIG. 2, apparatus 10 comprises an integrating chamber 18 for containing particles 17. Integrating chamber 18 is shown more particularly in FIG. 2 and has a plurality of interior walls. Integrating chamber 18 is elongated in the longitudinal direction, has a longitudinal axis and is generally horizontally symmetric about its longitudinal axis. In the first embodiment of the present invention, integrating chamber 18 contains and transports the particles.

Integrating chamber 18 includes an upper portion 18a and a lower portion 18b. In the first embodiment, upper portion 18a comprises a stationary cover. Upper portion 18a includes a narrow, light-admitting slot 20 for admitting light into chamber 18. The interior walls of upper portion 18a are coated with a material to efficiently and diffusely reflect and scatter any light striking them. A nearly lambertian, diffusely reflective, light-scattering material, sold under the trademark "DURAFLECT", and available from Labsphere, Inc. of North Sutton, N.H., has been found suitable for this purpose. The interior walls of lower portion 18b are also coated with a durable material having optical properties similar to those of the upper portion. A nearly lambertian, diffusely reflective, light-scattering material, such as diffusely reflecting polytetrafluoroethylene plastic, sold under the trademark "SPECTRALON", also available from Labsphere, Inc. has been found suitable for use with the present invention. The plastic coating is attached to the lower portion using an adhesive, such as a silicone adhesive or epoxy cement.

Lower portion 18b of integrating chamber 18 forms the trough of an oscillating feeder assembly, also known to one skilled in the art as a vibratory feeder. A suitable assembly for the oscillating feeder assembly of the first embodiment is commercially available as Model 20A from Eriez Magnetics of Erie, Pa. Lower portion 18b is mounted on elastic supports, not shown. Lower portion 18b is driven in an oscillatory motion by a motor 22 as shown in FIG. 2, which may be a reciprocating piston motor. When the motor piston reciprocates, lower portion 18b moves in an oscillatory fashion, primarily along the longitudinal axis of the integrating chamber, but with a small component of vertical motion. The motor and thus the lower portion typically oscillate with an amplitude of about one millimeter, at a frequency of about sixty Hertz. Lower portion 18b is horizontally symmetrical about the longitudinal axis of integrating chamber 18. Lower portion 18 includes a substantially planar surface 18b' for containing and transporting the particles. Planar surface 18b' has a longitudinal axis P as shown in FIG. 2 substantially parallel to the longitudinal axis of the integrating chamber and may be positioned such that it is level or inclined at an angle of up to 10° along its longitudinal axis. The particles of material are uniformly distributed along planar surface 18b'. The motor drives the trough in an oscillatory manner along the longitudinal axis so that the particles are transported through the chamber along the planar surface of the lower portion, primarily due to the oscillatory motion of lower portion 18b and, if the lower portion is inclined, due to gravity.

Figure 2A:
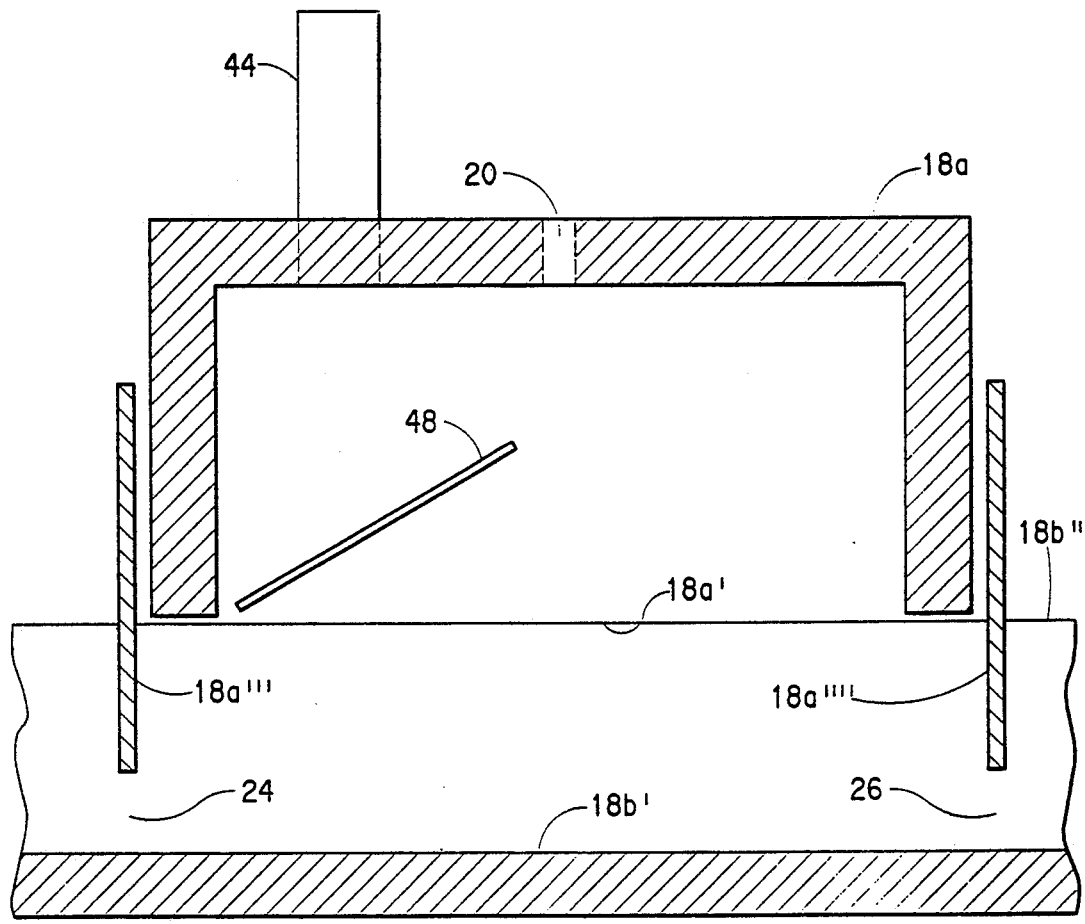
FIG. 2A is a longitudinal, cross-sectional view of the integrating chamber of the present invention taken across lines 2A—2A of FIG. 2.

Upper portion 18a and lower portion 18b of integrating chamber 18 are constructed and mounted so that there is sufficient clearance therebetween to allow the particles to pass unobstructed through the chamber. Each of the upper portion and the lower portion includes an upper peripheral edge and a lower peripheral edge which overlap in the vertical direction. Specifically, the lower peripheral edge of upper portion 18a overlaps the upper peripheral edge of lower portion 18b. The lower peripheral edges of upper portion 18a include a first lower peripheral edge 18a' and a second lower peripheral edge 18a". The upper peripheral edge of lower portion 18b includes a first upper peripheral edge 18b" and a second upper peripheral edge 18b"'. As shown in FIG. 2, an inlet hopper 19 is provided adjacent motor 22 for delivering particles of the material to lower portion 18b. An inlet opening 24 and an outlet opening 26, which are shown in FIG. 2A, are formed at the longitudinal ends of the chamber by planar surface 18b' of lower portion 18b and lower peripheral edges 18a' and 18a", respectively, of upper portion 18a. A flow-regulating gate 23 may be disposed above planar surface 18b' of lower portion 18b between hopper 19 and inlet opening 24 of integrating chamber 18. Flow-regulating gate 23 is manually adjustable by adjusting a knob 23a. Flow-regulating gate 23 ensures that a uniform layer of controlled thickness of material is spread along planar surface 18b' of lower portion 18b. The particles of material pass through inlet opening 24 as they enter integrating chamber 18 and through outlet opening 26 as they exit the chamber to a receptacle 27, which catches the particles as they exit integrating chamber 18.

It should be noted that the total area of the light-admitting slot and the inlet and outlet openings in the integrating chamber must be kept to a minimum for the integrating chamber to function in an optically efficient manner. The total area of the light-admitting slot and the inlet and outlet openings is typically only several percent of the total interior area of the integrating chamber. If desired, this percentage may be reduced by making the integrating chamber larger. In addition, the upper portion of the chamber is constructed with a first and a second descending end portion, 18a''' and 18a'''', respectively, at the longitudinal ends of the integrating chamber as shown in FIGS. 2 and 2a which reduce the height of inlet opening 24 and outlet opening 26, thereby minimizing light leakage from the integrating chamber.

Further in accordance with the first embodiment of the present invention, the apparatus for optically detecting light-absorbing contamination also comprises a laser 34 for emitting a laser beam to illuminate the at least one particle. Laser 34 is mounted in enclosure 16a as shown in FIG. 1. Laser 34 emits a laser beam, which is either reflected by or transmitted through the particles. The laser used in the first embodiment of the present invention is a commercially available, off-the-shelf item. An example of a laser suitable for use with the present invention is a helium neon laser, Model 05LHR321 manufactured by Melles Griot of Irvine, Calif. The laser of this model emits a beam that has low divergence and is substantially monochromatic, at a wavelength of 632.8 nanometers. Alternatively, lasers operating at other visible or infrared wavelengths, such as an argon-ion laser which operates at 457 nanometers, a diode laser which operates in the range of 670–950 nanometers or a neodymium-YAG laser which operates at 1064 nanometers, may be used. Laser 34 preferably includes a telescopic lens assembly 36 for collimating and expanding the laser beam. A suitable telescopic lens assembly for use with the first embodiment of the present invention, such as a Model 09LBM011 from Melles Griot, is used to expand and collimate the laser beam to a diameter of about three millimeters.

In the first embodiment, the apparatus for optically detecting light-absorbing contamination also comprises a scanning assembly mounted in optical alignment with the laser for reflecting the laser beam and for causing the laser beam to scan the particle in the optical integrating chamber. In the first embodiment, the scanning assembly includes a rotating mirror 28 mounted adjacent the integrating chamber as shown in FIG. 2. Mirror 28 has at least one reflective face disposed about the circumference thereof and an axis of rotation generally perpendicular to the reflective face. The axis of rotation of mirror 28 is substantially parallel to the longitudinal axis of the integrating chamber and is substantially orthogonal to planar surface 18b' of lower portion 18b. The scanning assembly in accordance with the first embodiment of the present invention also comprises a motor drive 30 and a shaft 32 as shown in FIG. 2. Mirror 28 is rotatably supported on shaft 32 and is rotatable about its axis of rotation by the motor. A beam folding mirror 35 is provided in the path of laser 34 to direct the laser to face 29 of mirror 28. As can be seen from FIG. 2, laser 34 is mounted in the plane of the rotation of rotating mirror 28 such that the laser beam reflects from the reflective surface of the rotating mirror and scans in a fan scan. The scan is oriented in a direction substantially perpendicular to the planar surface of lower portion 18b of the integrating chamber. The scanning assembly used in the first embodiment of the present invention is a commercially available, off-the-shelf item. A scanning assembly suitable for use with the first embodiment of the present invention is a Model M225-015-XLIM, available from Lincoln Laser Company of Phoenix, Ariz. Alternatively, in the first embodiment of the present invention, the scanning assembly could be a galvanometer-driven, rotating mirror, a resonant torsional scanner, a holographic scanner or an accousto-optic deflector.

The apparatus for optically detecting light-absorbing contamination in particles of the first embodiment also comprises a focusing assembly mounted in optical alignment with the laser for focusing the scanning laser beam onto the at least one particle in the chamber. The focusing assembly operates in conjunction with the scanning assembly so that light from the laser beam is reflected from the particles and is repeatedly scattered onto the interior walls of the integrating chamber. In accordance with the first embodiment of the present invention, the focusing assembly comprises a scan lens 38 disposed in enclosure 16a of framework 16. As can be seen more particularly in FIG. 2, scan lens 38 is mounted between integrating chamber 18 and rotating mirror 28. Scan lens 38 converts the fan scan into a telecentric scan and focuses the scanning laser beam onto the particles in integrating chamber 18. Scan lens 38 operates in conjunction with the scanning assembly so that light from the laser is reflected from the particle and is repeatedly scattered onto the interior walls of the integrating chamber. The vertical position of scan lens 38 is adjustable relative to integrating chamber 18 in order to accurately adjust the telecentric scan. Thus, the laser beam stays uniformly focused across the entire width of lower portion 18b. A scan lens suitable for use with the first embodiment of the present invention is a 227 millimeter diameter, 526 millimeter focal length scan lens, available as Part Number SN72055 from Edmund Scientific Company of Barrington, N.J. Alternately, an f-theta lens may be used to cause the focused scanning laser beam to scan in an f-theta pattern. Scan lens 38 is mounted with respect to rotating mirror 28 so that the scanning collimated beam passes through the lens along the central chord of the lens. Since the laser beam is collimated as it passes the first focal plane of the lens, the lens causes the beam to focus at the second focal plane of the lens. The apparent origin point of the scanning beam is at the first focal plane of the lens, and thus the lens converts the fan scan into a telecentric scan. The telecentric scan maintains a constant incidence angle of the scanning laser beam onto the particles to ensure that the sensitivity of the apparatus to contaminants is uniform across the width of lower portion 18b. Alternatively, the focusing assembly may comprise a telescopic lens assembly mounted between the laser and the scanning assembly. In this alternate arrangement, the scan lens is omitted. The telescopic lens assembly is adjusted to focus the laser beam at the particles on the planar surface of the integrating chamber. In such an arrangement, the distance between the rotating mirror and the particles on the surface must be sufficiently large to minimize the effect of the arcuate beam path on the focus of the laser beam.

The scanning assembly, the laser, the telescopic lens assembly, the beam-folding mirror and the scan lens are enclosed in enclosure 16a of framework 16 as shown in FIG. 1 to prevent external light from entering the apparatus and to keep dirt out of the system. A suitable enclosure is a NEMA-4 enclosure available from Hoffman Engineering Company of Anoka, Minn. as Model D-L48H3616LPB. A light exit slot formed in the bottom surface of enclosure 16a allows the beam to exit enclosure 16a and to enter light-admitting slot 20 of upper portion 18a of integrating chamber 18.

In accordance with the first embodiment of the present invention, the apparatus of the present invention also comprises a laser beam position indicating assembly mounted in a fixed relationship to the scanning assembly for detecting when the scanning laser beam reaches a predetermined point and for generating a scan detection signal in response thereto. Preferably, the laser beam position indicating assembly of the first embodiment comprises a photodetector assembly 40 mounted in a fixed relationship to the scanning assembly, or specifically, in this embodiment, to rotating mirror 28. Alternatively, the laser beam position indicating assembly may comprise a magnetic detector for detecting the angular position of the scanning assembly as shown at 41 in FIG. 2. As can be seen in both FIGS. 1 and 2, photodetector assembly 40, also called a start of scan detection assembly, is mounted adjacent to integrating chamber 18 in enclosure 16a. In this context, adjacent may mean either in, on or near. Photodetector assembly 40 includes a photodetector 40a and a scan detection circuit 40b. The photodetector of photodetector assembly 40 is preferably a photodiode which is split into a first and second portion. A suitable split photodiode for use as the photodetector of the laser beam position indicating assembly of the first embodiment of the present invention is available as Model SD-113-24-21-021 from Silicon Detector Corporation of Camarillo, Calif. Photodetector assembly 40 detects when the scanning laser beam reaches a predetermined point on photodetector 40a and generates a scan detection signal in response thereto. The scan detection signal has a leading edge which occurs when the laser beam has crossed the first portion of the split photodiode and begins to illuminate the second portion thereof and a trailing edge which occurs as the laser beam passes from the first portion.

Figure 3:
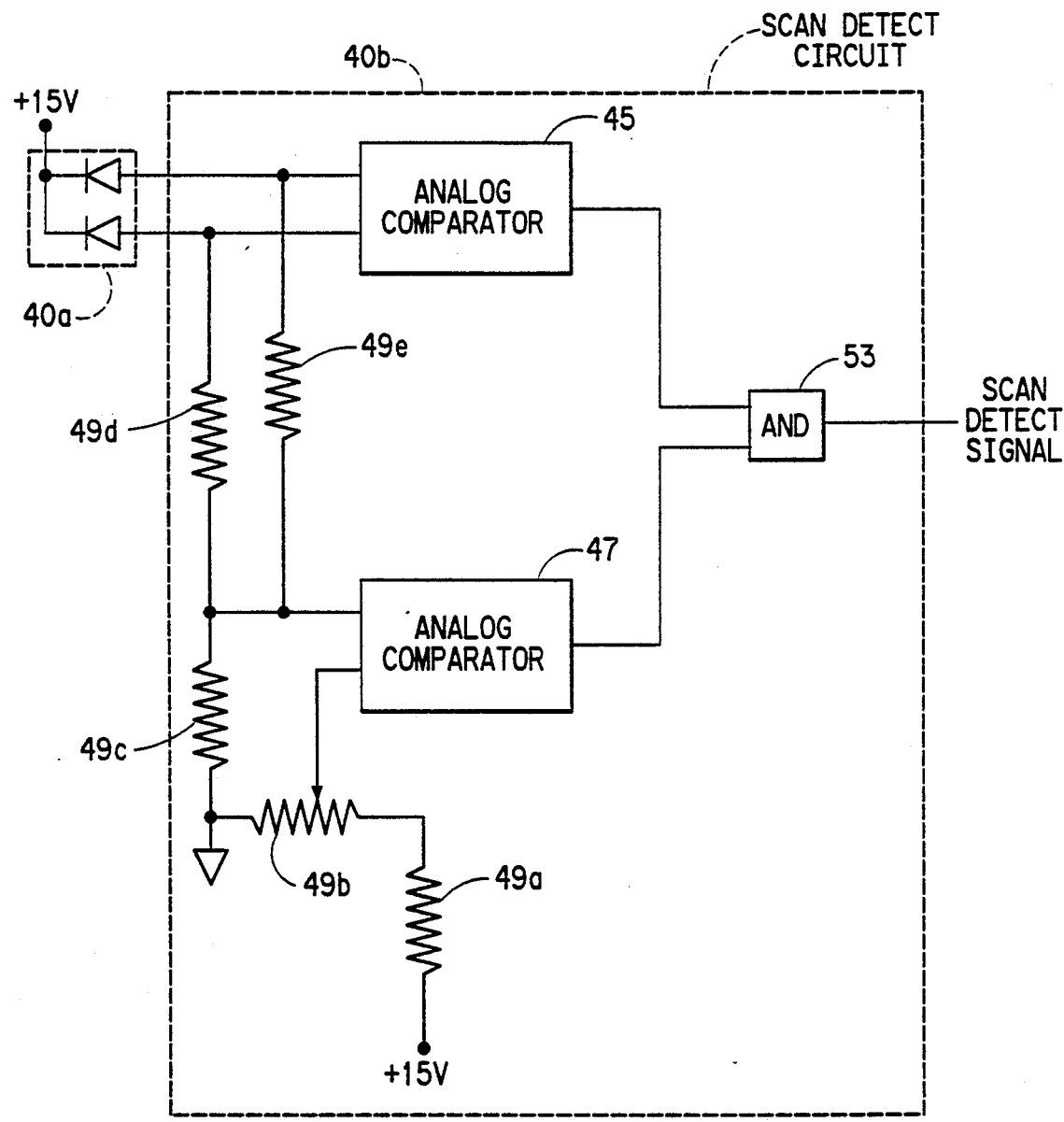
FIG. 3 is a block diagram of the scan detection circuit used with the first embodiment of the present invention.

The details of scan detection circuit 40b are shown in FIG. 3. Each portion of the split photodiode is biased by a DC voltage, typically +15 V supplied from a power supply in computer subsystem 14, and conducts electric current proportional to the intensity of the incident laser beam. The currents from each portion of the split photodiode are then sent to and compared by a first analog comparator 45, a second analog comparator 47 and a plurality of resistors 49a–49e. As the focused laser beam scans, it illuminates the first portion and then the second portion of the split photodiode. The output of first analog comparator 45 changes from an OFF state to an ON state when the input voltage resulting from the first portion of the photodiode exceeds the voltage resulting from the second portion of the photodiode. As the laser beam continues to scan across the boundary between the first and second portions of the split photodiode, the intensity of the light impinging on the first portion and the corresponding voltage resulting therefrom begins to drop. As the beam begins to illuminate the second portion, the light intensity impinging on the second portion of the split photodiode increases, and the voltage resulting therefrom increases. The output of second comparator 47 changes from an OFF state to an ON state when the input voltage exceeds the threshold voltage level created by the voltage divider formed by resistors 49a and 49b. When the light intensity on the first portion has dropped below that on the second portion, the output of first analog comparator 45 is changed to the OFF state. A logical AND gate 53 receives the two output signals from first and second analog comparators 45 and 47, respectively. When both comparator outputs are ON, the output of the AND gate assumes the ON state, and the scan detect signal is generated.

Figure 5:
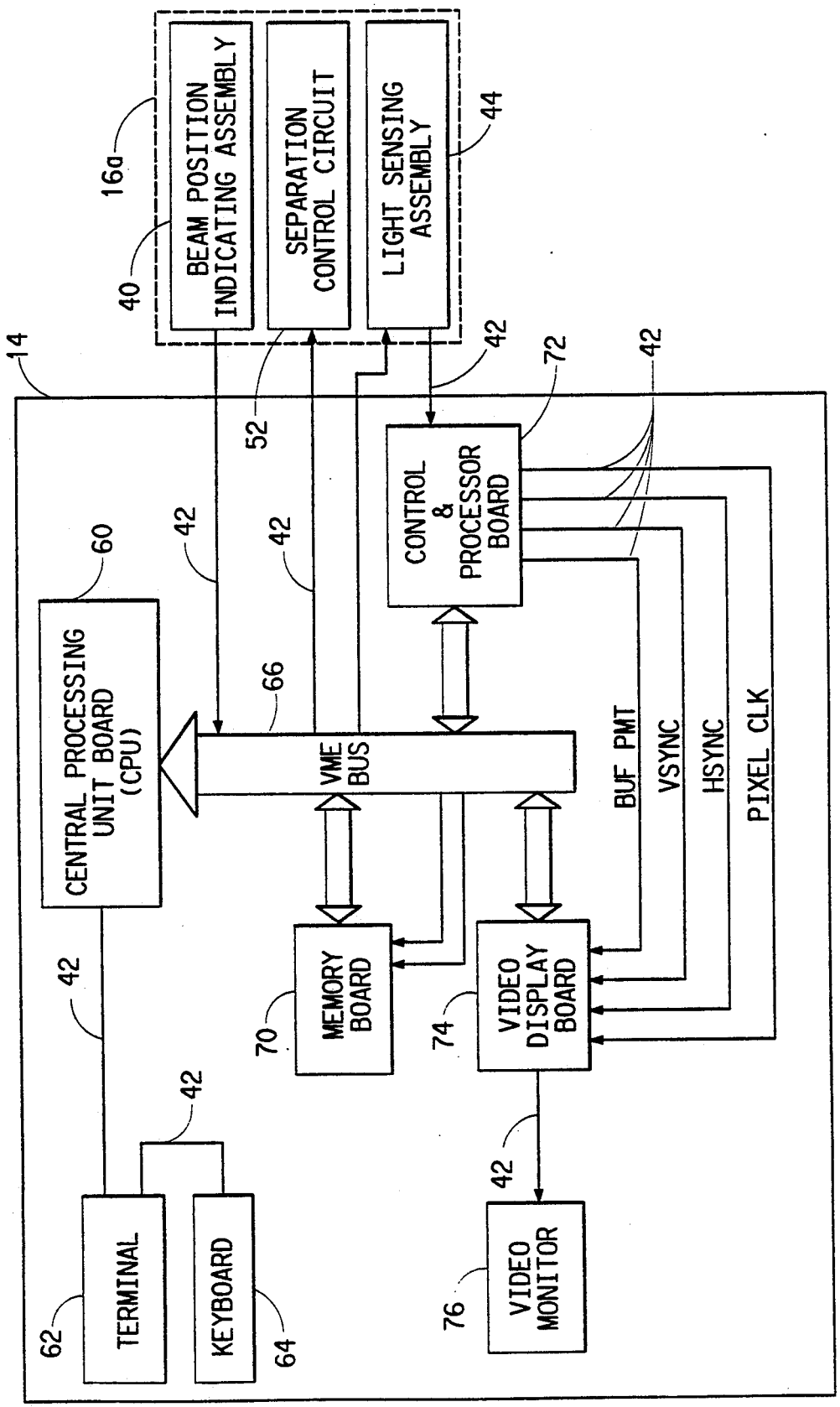
FIG. 5 is a system block diagram of the components of the computer subsystem of the apparatus of the first embodiment of the present invention.

The cables for connecting the components of optical subsystem 12 to computer subsystem 14, and the components of computer subsystem 14 to each other, are all designated by reference numeral 42. The scan detect signal generated by the scan detection circuit of photodetector assembly 40 as shown in FIG. 3 is transmitted via cable 42 to computer subsystem 14 as shown in FIGS. 1, 2 and 5.

Figure 8:
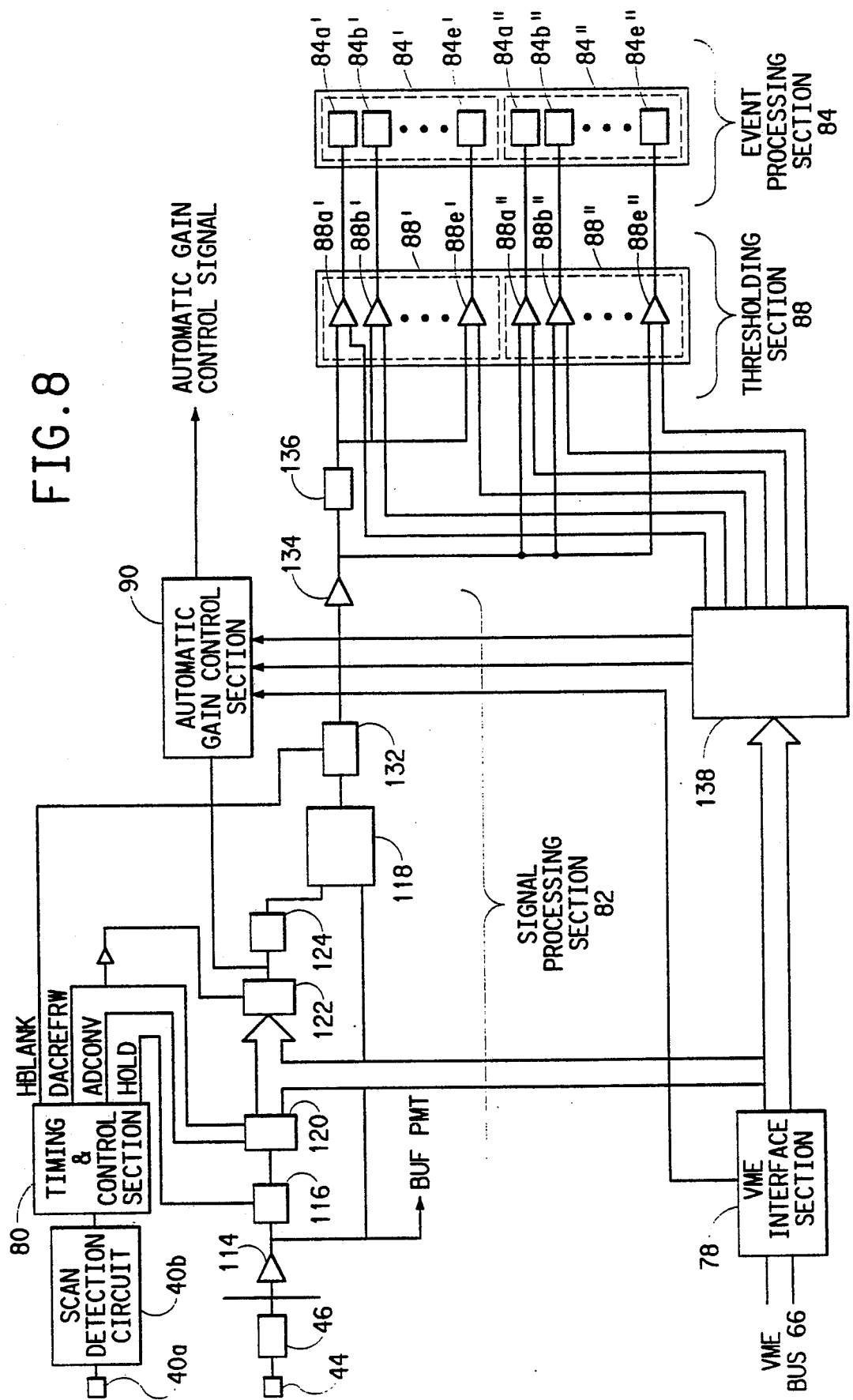
FIG. 8 is a system block diagram of the components of the signal processing section of the control and processor board as shown in FIGS. 5 and 6 and their relationship to the timing and control section, the automatic gain control section, the thresholding section and the event processor section of the control and processor board.

The apparatus of the first embodiment of the present invention also comprises a light sensing assembly for generating an intensity signal indicative of the intensity of the repeatedly scattered light, wherein a decrease in the intensity of the repeatedly scattered light is a function of the presence of light-absorbing contamination in the material. The light sensing assembly comprises a photodetector assembly mounted adjacent the integrating chamber for receiving light repeatedly scattered in the chamber. In this context, adjacent may mean either in, on or near. In the first embodiment, the light sensing assembly comprises a photodetector assembly 44 as shown in FIGS. 1, 2 and 8. As can be seen in both FIGS. 1 and 2, photodetector assembly 44 is mounted on upper portion 18a of integrating chamber 18, and upper portion 18a is constructed with an opening for photodetector assembly 44 to extend therethrough. Photodetector assembly 44 of the first embodiment preferably includes a photomultiplier tube and a high voltage power supply for the photomultiplier tube. A suitable photomultiplier tube for use with the present invention is Model 8654 from Burle Industries of Lancaster, Pennsylvania. A high voltage power supply suitable for use with the present invention is Model PMT-10C/N from Bertan Associates, Inc. of Hicksville, N.Y. Although a photomultiplier tube is used with the present invention, alternatively, the light sensing assembly may comprise another type of photodetector, such as a photodiode or a vacuum photodiode.

Figure 6:
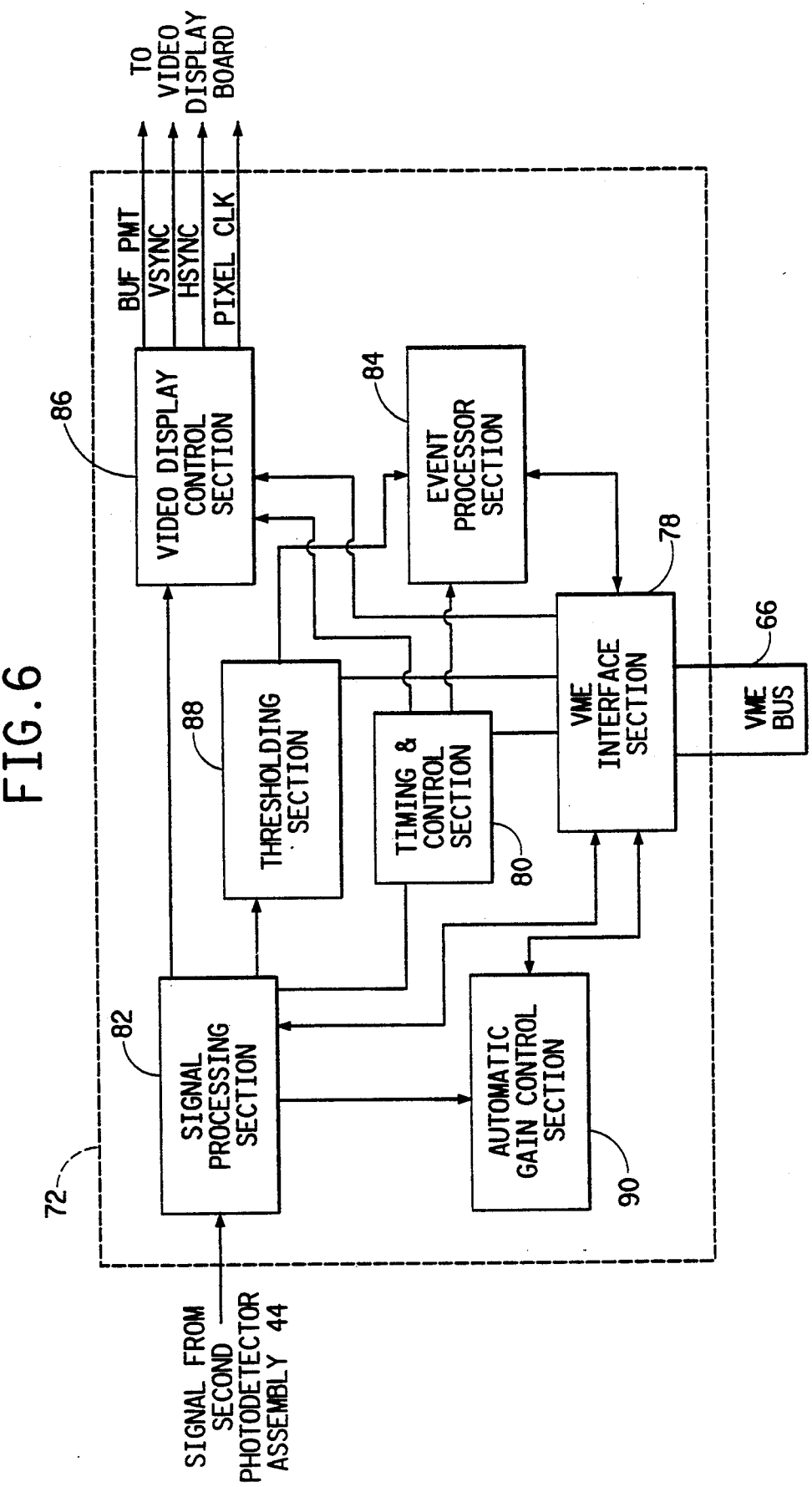
FIG. 6 is a system block diagram of the control and processor board of the computer subsystem of the first embodiment of the present invention as shown in FIG. 5.

Photodetector assembly 44 receives light repeatedly scattered in the chamber and produces an intensity signal, which is transmitted via cable 42 to a preamplifier. The preamplifier is part of a preamplifier module 46 as shown in FIGS. 2 and 6. Preamplifier module 46 amplifies the intensity signal generated by photodetector assembly 44 and converts it into a voltage, which is transmitted to computer subsystem 14. An optical filter (not shown), which passes substantially only the laser wavelength, can be mounted in front of photodetector assembly 44 to reduce the amount of ambient or background light entering inlet opening 24 or outlet opening 26 and reaching photodetector assembly 44, thereby improving the signal-to-noise ratio of the intensity signal.

The intensity of the light reflected from or passing through the particle is a function of the optical properties of the particle at that point. If the material has low optical-loss properties, that, it is highly transparent or highly reflective, then any light striking the particle will be repeatedly scattered from the interior walls of the integrating chamber. The intensity signal generated by photodetector assembly 44 is indicative of intensity of the light repeatedly scattered from the interior walls of the integrating chamber. If the area of the integrating chamber which is illuminated by the laser beam contains contaminated particles or contaminants which absorb a portion of the incident scanning laser beam, then the resulting amplitude of the signal from photodetector assembly 44 decreases. If that area contains uncontaminated particles or no contaminants, then little light is absorbed, and the resulting amplitude of the signal from photodetector assembly 44 remains substantially unchanged. Moreover, if the material of the particle to be inspected has low optical-loss properties, then the shape of the particle has very little effect on the intensity of the light received by photodetector assembly 44, since only repeatedly scattered light reaches this photodetector assembly. Since substantially all the light emerging from the particles is collected, and the light emerging at all angles contributes equally to the light reaching photodetector assembly 44, the apparatus according to the present invention is highly sensitive to local variations in light absorption in the particles and is only very slightly sensitive to the shape or orientation of the particles.

In accordance with the first embodiment of the present invention, the apparatus of the present invention may also comprise a baffle mounted inside the integrating chamber to ensure that only repeatedly scattered light is incident on the photodetector assembly of the light sensing assembly. In the first embodiment, at least one light baffle 48 is mounted in upper portion 18a of integrating chamber 18, preferably between the area illuminated and photodetector assembly 44, as shown in FIG. 2 and ensures that only light which has been repeatedly scattered can reach the photodetector assembly. The surfaces of the light baffle have the same optical properties (i.e., nearly lambertian, diffusely reflective and light-scattering) as the other interior surfaces of the integrating chamber. When particles having planar surfaces, such as polymer cubes, are scanned, the baffle prevents specularly reflected light from these surfaces from impinging directly on photodetector assembly 44, thereby causing light intensity variations, which are a function of particle orientation rather than particle light absorption. Such light intensity variations would produce a "noise" component in the signal from the photodetector assembly of the light sensing assembly, which would degrade the ability of the system to detect the presence of contaminants. If the particles being scanned do not have planar surfaces or are sufficiently lambertian in their light-scattering characteristics, baffle 48 may be omitted.

Figure 4:
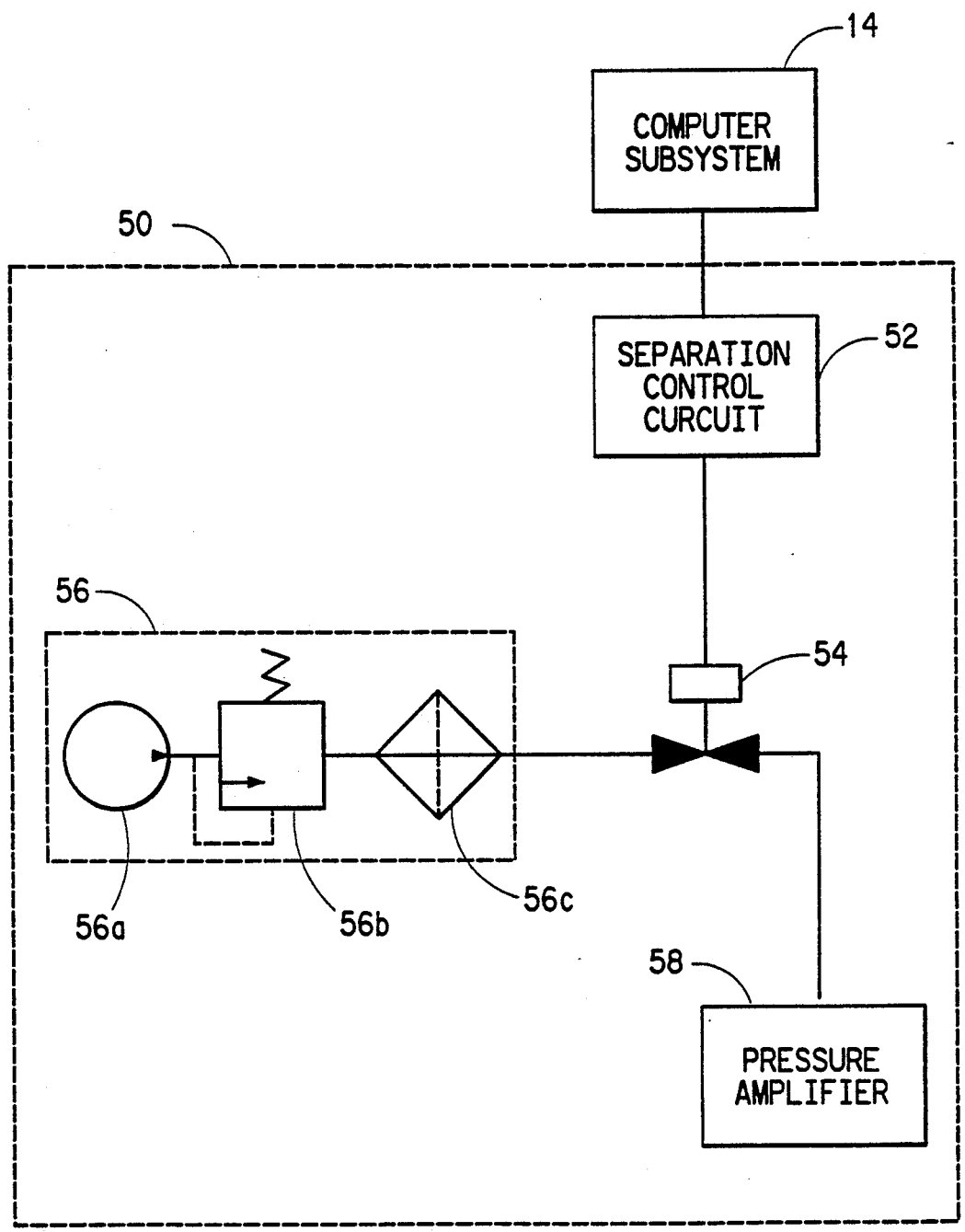
FIG. 4 is a schematic view of the subsystem for separating contaminated particles of the apparatus according to the first embodiment of the present invention.

The apparatus of the present invention also comprises a subsystem for separating the contaminated particles from the material in the integrating chamber in response to a separation control signal from the computer subsystem. The subsystem for separating the contaminated particles is shown generally at 50 in FIG. 2, and the details of the subsystem are shown in FIG. 4. As can be seen from FIG. 4, the separation subsystem includes a separation control circuit 52. Separation control circuit 52 is preferably a solid-state relay which controls the operation of a solenoid valve 54. When a contaminant is detected, computer subsystem 14 generates a separation control signal to activate separation control circuit 52. Separation control circuit 52 causes solenoid valve 54 to open. Solenoid valve 54 is typically open for a small fraction of a second when a contaminant is detected. Solenoid valve 54, when open, allows the air from a pressurized air supply, which is shown generally at 56 in FIG. 4 and includes a pressurized air supply 56a, a regulator 56b and a filter 56c, to pass to a pressure amplifier 58. Pressure amplifier 58 is used to create a suction, which causes all the particles in the vicinity of the contaminant to be separated from the normal flow of the particles along the lower portion of the integrating chamber.

FIG. 5 is a simplified block diagram of the computer subsystem of the present invention shown generally at 14 in FIG. 1. Referring to FIG. 5, computer subsystem 14 includes a Central Processor Unit (CPU) board 60 for controlling the computer subsystem. Specifically, the CPU board generates control and data signals in response to a compiled computer program stored in a Read Only Memory (ROM), which may be located on the CPU board. Alternatively, the ROM may be on a separate support board. Cables 42 transmit the control and data signals between the components of computer subsystem 14 as shown in FIG. 5. A CPU board suitable for use with the present invention is Model SYS68K/-CPU-29 from Force Computers, Inc. of Los Gatos, Calif.

CPU board 60 is connected by cable 42 to a terminal 62, which includes a keyboard 64. Terminal 62 allows the user to control operation of the apparatus by interacting with CPU board 60. A terminal used with the computer subsystem of the present invention is typically Model 330 from Digital Equipment Corporation of Maynard, Mass., which includes a video monitor and a keyboard.

CPU board 60 is connected to the rest of the computer subsystem via a VME bus 66. VME bus 66 transmits the control and data signals generated by CPU board 60 to the other boards in computer subsystem 14 as shown in FIG. 5. In addition, VME bus 66 is connected to photodetector assembly 40, photodetector assembly 44 and separation subsystem 50, which are all mounted in enclosure 16a as shown in FIG. 5.

VME bus 66 is connected to a memory board 70. Memory board 70 may contain a Random Access Memory (RAM), or a non-volatile RAM or ROM, or a combination thereof. Memory board 70 stores data from CPU board 60 received via VME bus 66. A memory board suitable for use with the present invention is a RAM board, Model VME 9100D, from Logical Design Group, Inc. of Raleigh, N.C.

The apparatus of the present invention also includes a signal processing assembly connected to the photodetector assembly of the light sensing assembly for amplifying and filtering the intensity signal. The signal processing assembly includes a control and processor board 72 which is connected by cable 42 to photodetector assembly 44 for receiving, amplifying and filtering the signal generated by photodetector assembly 44. Control and processor board is also connected to CPU board 60 via VME bus 66.

The apparatus of the present invention further includes a video display section connected to the signal processing assembly for displaying the amplified and filtered signal. In the first embodiment, the video display section comprises a display board 74 and a video monitor 76 which displays the amplified and filtered signal in the form of an image as shown in FIG. 5. A video display board suitable for use with the present invention is Model DT1451 from Data Translation of Marlboro, Mass. A video monitor suitable for use with the present invention is Model TC1910A from Burle Industries of Lancaster, Pa. As shown in FIG. 5, CPU board 60 is connected, via VME bus 66, to video display board 74. Video display board 74 is connected, in turn, to control and processor board 72 via four cables 42. Each of these cables transmits a different signal, specifically, a BUF PMT signal, and three synchronization signals, VSYNC, HSYNC and PIXEL CLK, as shown in FIG. 5. The BUF PMT signal is a buffered copy of the signal generated by photodetector assembly 44. Video display board 74 digitizes and stores the BUF PMT signal from control and processor board 72 and formats the stored BUF PMT signal for display. Video display board 74 also receives the synchronization signals VSYNC, HSYNC and PIXEL CLK via cables 42 from control and processor board 72. These signals control the rate at which the video display board digitizes and formats the BUF PMT signal. Video display board 74 is connected by cable 42 to video monitor 76 and converts the digitized and formatted signal into an RS-170 standard video signal, which it sends to video monitor 76. Video monitor 76 provides a pictorial display of the particles being scanned from the video signal.

FIG. 6 is a system block diagram of control and processor board 72. As shown in FIG. 6, control and processor board 72 includes a VME interface section 78 which is connected to VME bus 66. VME interface section interprets the control and data signals from CPU board which are transmitted to and from CPU board 60 on bus 66. The VME interface section is implemented with a programmable circuit, such as Model 5128-2 from Altera Corporation of Santa Clara, Calif.

VME interface section 78 also connects to a timing and control section 80, which generates timing signals in response to the trailing edge of the scan detect signal generated by photodetector assembly 40 in accordance with the control and data signals from CPU board 60. The details of timing and control section 80 will be described below with reference to FIG. 7. The timing and control section is also implemented with a programmable circuit, such as Model 5128-2 used for the VME interface section as described above. The timing and control signals include a HOLD signal, an ADCONV signal, a DACREFRW signal and an HBLANK signal, as shown in FIGS. 7 and 8.

The timing and control signals, in turn, control a signal processing section 82. Signal processing section 82 generates a pedestal reference signal which occurs when a point on the integrating chamber known to contain no particles is illuminated by the laser beam. The pedestal reference signal, in digital form, is sent to VME interface section 78 so that it can be read out or controlled by CPU board 60. The timing and control signals also control an event processor section 84 which counts the number of contaminants detected by the apparatus. The counts accumulated by event processor section 84 are read out by VME interface section 78. The timing and control signals are also processed by a video display control section 86 to generate the synchronization signals, VSYNC, HSYNC and PIXEL CLK as shown in FIG. 5 and which are required by video display board 74. The synchronization signals are synchronized to the scan detect signal generated by photodetector assembly 40. The manner in which the timing and control signals are processed by video display control section 86 is controlled by the control and data signals sent by CPU board 60 via VME interface section 78. VME interface section 78 also connects to a thresholding section 88, which compares the signal level of the processed video signal from signal processing section 82 to a plurality of predetermined reference voltage levels. These predetermined reference voltage levels are set in response to the control and data signals from CPU board 60.

Figure 9:
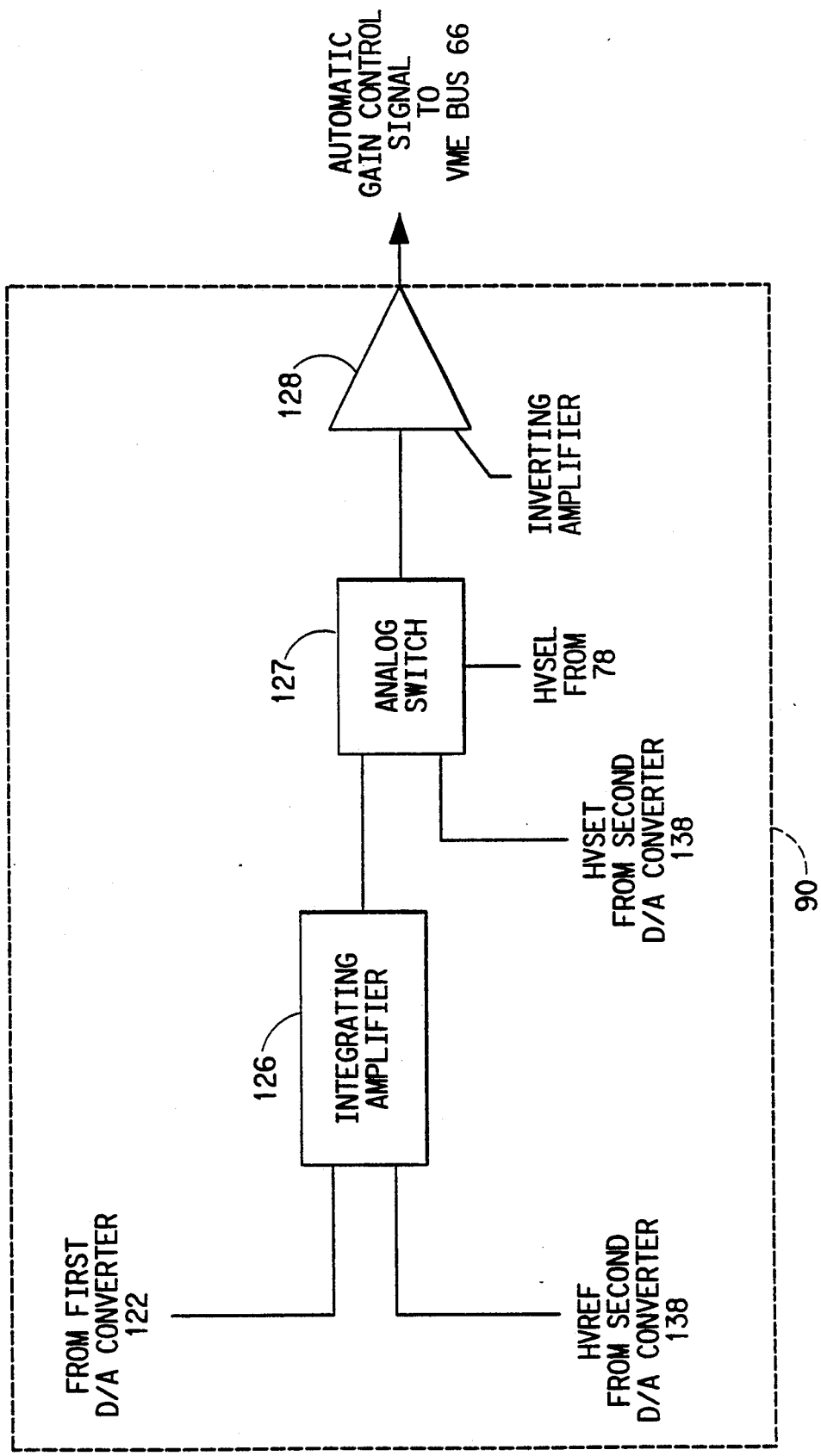
FIG. 9 is a system block diagram of the automatic gain control section of the control and processor board as shown in FIGS. 5 and 6.

The apparatus of the present invention also includes an automatic gain control section 90 as shown in FIGS. 6, and 9 connected to the signal processing assembly for generating a control signal in response to changes in at least one of the amount of optical power entering the chamber from the laser, the scattering efficiency of the integrating chamber or the sensitivity of photodetector assembly 44. VME interface section 78 is also connected to an automatic gain control section 90. Automatic gain control section 90 receives the pedestal reference signal from signal processing section 82. Automatic gain control section 90 generates an automatic gain control signal which is transmitted to the high voltage power supply of photodetector assembly 44 via VME bus 66 and cables 42. The automatic gain control signal thus controls the sensitivity of photodetector assembly 44 in response to variations in the pedestal reference signal caused by changes in any of the following factors, either alone or in combination: the amount of optical power entering the chamber from the laser, the scattering efficiency of the integrating chamber or the sensitivity of the photodetector assembly of the light sensing assembly.

Figure 7:
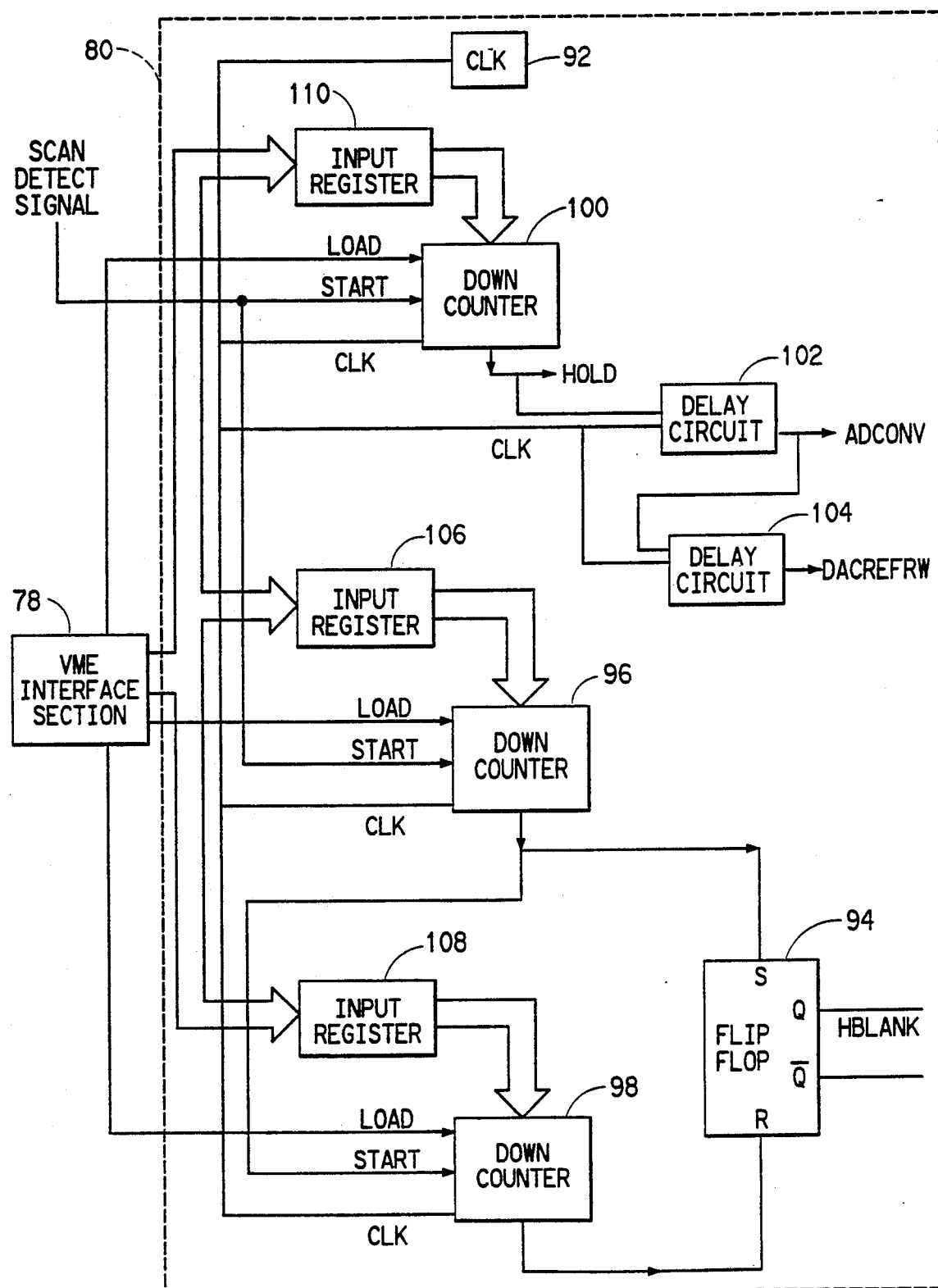
FIG. 7 is a system block diagram of the timing and control section of the control and processor board as shown in FIGS. 5 and 6.

FIG. 7 is a block diagram showing the components of timing and control section 80. Timing and control section 80 generates control signals for signal processing section 82 and for automatic gain control section 90. Timing and control section 80 includes a crystal-controlled clock 92, a flip-flop 94, a first, a second and a third down counter 96, 98 and 100, respectively, a first and a second delay circuit 102 and 104, respectively, and a first, a second and a third input register 106, 108 and 110, respectively. The output of clock 92 is sent to the clock (CLK) input of down counters 96, 98 and 100, respectively. The scan detect signal is sent to the start inputs of first and third down counters 96 and 100, respectively. A predetermined time delay for each down counter 96, 98 and 100 is set by CPU board 60 via VME interface section 78 and is stored in input registers 106, 108 and 110, respectively. The output of down counter 96 initiates down counter 98. The respective outputs of down counters 96 and 98 set and reset flip-flop 94 to generate the HBLANK signal. Down counter 100 is used to generate the HOLD signal. Down counter 100 is also used in combination with first delay circuit 102 to generate the ADCONV signal and further in combination with second delay circuit 104 to generate the DACREFRW signal.

FIG. 8 is a block diagram primarily showing the components of signal processing section 82 and their relationship to timing and control section 80, automatic gain control section 90, thresholding section 88 and event processor section 86 of control and processor board 72. As shown in FIG. 8, signal processing section 82 is connected to photodetector assembly 44 via preamplifier module 46 and to timing and control section 80, which in turn is connected to photodetector assembly 40. The HBLANK, DACREFRW, ADCONV and HOLD signals generated by timing and control section 80 in response to the scan detect signal generated by first assembly 40 are transmitted to signal processing section 82 as shown in FIG. 8. Signal processing section 82 is also connected to automatic gain control section 90 for controlling the automatic gain control signal and to thresholding section 88 as shown in FIG. 8. The output of thresholding section 88 is sent to event processor section 84.

Referring to the details of FIG. 8, signal processing section 82 includes a first noninverting buffer amplifier 114 for buffering the input signal received from preamplifier module 46. This buffered signal is the BUF PMT signal as described above with respect to the description of FIG. 5. The output of first buffer amplifier 114 is connected to a sample and hold amplifier 116 and to an amplifier 118. A sample and hold amplifier suitable for use with the present invention is Model CLC940 from Comlinear Corporation of Fort Collins, Colo. Sample and hold amplifier 116 samples the BUF PMT signal from amplifier 114 under control of the HOLD signal generated by timing and control section 80.

The output of sample and hold amplifier 116 is sent to an analog-to-digital (A/D) converter 120. A/D converter 120 converts the incoming analog signal from sample and hold amplifier 116 to digital form in response to the ADCONV signal generated by timing and control section 80. The ADCONV signal is the second signal in the automatic gain control sequence, the HOLD signal being the first. A/D converter 120 outputs the digital representation of the held signal from sample and hold amplifier 116 in response to the DACREFRW signal which is generated by timing and control section 80. The DACREFRW signal is the third signal in the automatic gain control sequence. An A/D converter suitable for use with the present invention is model ADC774 from Burr-Brown Corporation of Tuscon, Ariz.

The output of A/D converter 120 is sent to the data input of a first digital-to-analog (D/A) converter 122 and to VME interface section 78. Timing and control section 80 provides the inverted version of the DACREFRW signal to first D/A converter 122. First D/A converter 122 captures the data from A/D converter 120 in response to the inverted DACREFRW signal. Alternatively, VME interface section 78 can provide the data input for first D/A converter 122. A D/A converter suitable for use with the present invention as first digital-to-analog converter is model AD767 from Analog Devices of Norwood, Mass.

The output signal of first D/A converter 122 is sent to a first low-pass filter 124 as shown in FIG. 8. First low-pass filter 124 removes small variations in the signal provided by first D/A converter 122. The output of first low-pass filter 124 is sent to the input of amplifier 118. Amplifier 118 inverts the sum of the filtered digital-to-analog signal output from first low-pass filter 124 and the output from first buffer amplifier 114. The output signal of first D/A converter 122 is also sent to an integrating amplifier 126 of automatic gain control section 90 as shown in FIG. 9. FIG. 9 is a block diagram showing the components of automatic gain control section 90. Automatic gain control section 90 comprises an integrating amplifier 126, a first analog switch 127 and an inverting amplifier 128.

The apparatus of the present invention also includes a digital-to-analog converter connected to the automatic gain control section for generating a plurality of DC reference voltages. Referring to FIG. 8, a digital-to-analog (D/A) converter for generating a plurality of DC reference voltages is shown at 138. D/A converter 138 comprises a second D/A converter in the apparatus of the present invention and determines a voltage reference level, HVREF. Integrating amplifier 126 subtracts the signal provided by first D/A converter 122 from voltage reference level, HVREF, and integrates the difference. Second D/A converter 138 also generates a plurality of DC reference voltages, which are used by thresholding section 88 as described below. Second digital-to-analog (D/A) converter 138 is a multi-port D/A converter. A multi-port D/A converter suitable for use as second D/A converter is Model AD 722, which is commercially available from Analog Devices. In normal operation, first analog switch 127 conveys the output of integrating amplifier 126 to inverting amplifier 128. For trouble shooting, CPU board 60, via VME interface section 78, can assert an HVSEL signal, which allows the operator of the apparatus to manually control the operation of first analog switch 127. CPU board 60 also controls an HVSET signal which is generated by second D/A converter 138 and which can be used to set the high voltage level produced by the high-voltage power supply of photodetector assembly 44 to a predetermined level. Inverting amplifier 128 inverts the signal from analog switch 127 and controls the high voltage level.

The output of amplifier 118 is sent to a second analog switch 132 as shown in FIG. 8. The operation of analog switch 132 is controlled by the HBLANK signal generated by timing and control section 80. When the HBLANK signal is logic High, the switch is open, preventing the summed and inverted signal from automatic gain control section 90 from reaching the other circuitry. When the HBLANK signal is logic Low, the switch is closed, permitting a second noninverting buffer amplifier 134 to receive the summed and inverted signal.

The apparatus of the present invention also includes a thresholding section comprising a plurality of comparators for comparing the plurality of DC reference voltages to the amplified and filtered signal. A thresholding section is shown at 88 in FIG. 8. The output of second buffer amplifier 134 is sent to a thresholding group 88" of thresholding section 88 and to a second low-pass filter 136. Second low-pass filter 136 further processes the signal from second buffer amplifier 134 to remove high frequency components from the signal and provide amplification thereof. The filtered signal from second low-pass filter 136 is then sent to a thresholding group 88' of thresholding section 88. Thresholding section comprises a plurality of comparators for comparing the plurality of DC reference voltages to the amplified and filtered signal. In the preferred configuration of the first embodiment, there are two groups of five comparators, 88a'-8e' and 88a"-88e". Comparators 88a'-8e' are connected to the output of second low-pass filter 136, and comparators 88a"-88e" are connected to the output of second buffer amplifier 134. In the preferred embodiment, there are ten independently controlled reference voltage levels. Each output port of D/A converter 138 provides a reference voltage level to a respective comparator 88a'-88e' and 88a"-88e', Comparator 88a' compares the signal level received from second low-pass filter 136 to a first reference voltage level provided by second D/A converter 138 under the control of CPU board 60. Each successive comparator 88b'-88e' compares the signal level received from second low-pass filter 136 to a corresponding predetermined reference voltage level provided by second D/A converter 138 under the control of CPU board 60. Comparator 88a" compares the signal level received from second buffer amplifier 134 to a first reference voltage level provided by second digital-to-analog converter 138 under the control of CPU board 60 via VME interface section 78. Each successive comparator 88b"-88e" compares the signal level received from second buffer amplifier 134 to a corresponding predetermined reference voltage level provided by second D/A converter 138 under the control of CPU board 60. The output of comparators 88a"-88e" becomes logic-High when the signal from buffer amplifier 134 exceeds the corresponding reference voltage level. The output of comparators 88a'-88e' becomes logic-High when the filtered signal from second low-pass filter 136 exceeds the corresponding reference voltage level. The output of each comparator 88a'-88e' is sent to a respective event processor 84a'-84e' in event processor group 84' of event processor section 84, and the output of each comparator 88a'-88e" is sent to a respective event processor 84a"-84e" in event processor group 84" of event processor section 84.

Figure 10:
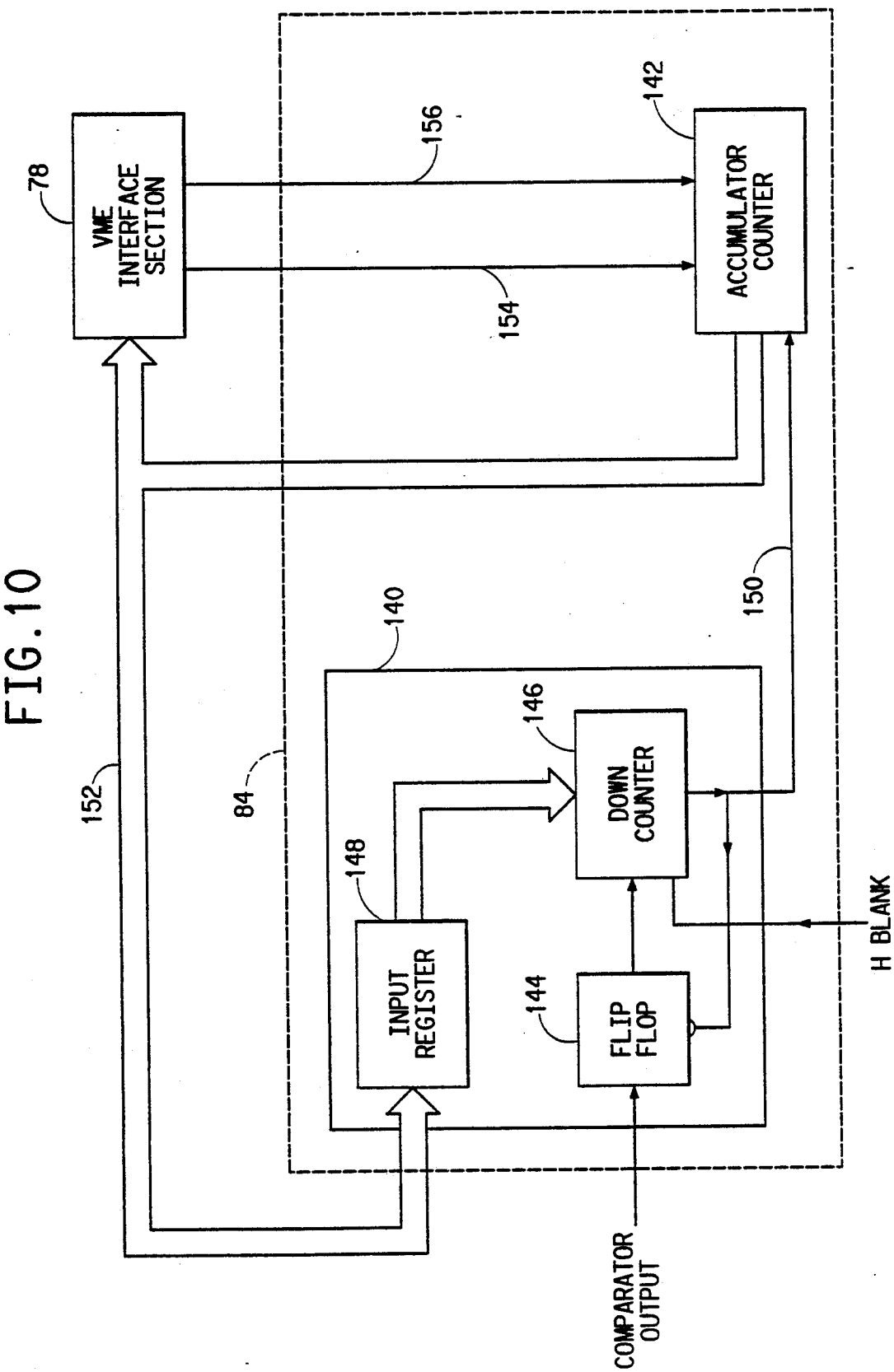
FIG. 10 is a system block diagram of the event processor section of the present invention as shown in FIGS. 6 and 8.

FIG. 10 is a block diagram showing the details of a single event processor in event processor section 84. Each event processor 84a'-84e' in group 84' counts the number of times that the signal from second low-pass filter 136 exceeds the reference voltage level provided by second D/A converter 138 under the control of CPU board 60. Each event processor 84a"-84e" in group 84" counts the number of times that the unfiltered signal from buffer amplifier 134 exceeds the predetermined reference voltage level provided by second D/A converter 138 under the control of CPU board 60. Each event processor in event processor group 84' and 84" comprises a delay circuit 140 and an accumulator counter 142. Delay circuit 140 comprises a flip flop 144, a fourth down counter 146 and an input register 148. The output signal from each comparator 88a'-88e' or 88a"-88e", which can be a very short duration pulse, is captured by flip flop 144. The output of flip-flop 144 enables fourth down counter 146, which counts a predetermined number of HBLANK signals and generates a single output pulse when the output of fourth down counter 146 reaches a count of zero. The output pulse is sent to accumulator counter 142 via line 150 and to the reset input of flip-flop 144. A predetermined number of HBLANK signals is set by CPU board 60 via VME interface section 78 and a data bus 152 and is stored in input register 148. VME interface section 78 also controls the operation of accumulator counter 142 and reads the accumulated count of contaminants counted by counter 142. VME interface section 78 is connected to accumulator counter 142 via data bus 152 and control lines 154 and 156. Control line 154 controls whether accumulator counter 142 counts up or down for each input pulse, and control line 156 resets accumulator counter 142 to zero. Data bus 152 allows VME interface section 78 and CPU board 60 to read the accumulator count. The number of counts accumulated is controlled by delay circuit 140 to reduce the likelihood that a single event will generate multiple counts.

The operation of the apparatus of the present invention will now be described with reference to the elements of the apparatus as described above. The apparatus of the present invention is assumed to be in an operational state, meaning that the laser is on, the rotating mirror is rotating, the lower portion of the integrating chamber is oscillating, and the computer subsystem is operating.

The particles of low optical-loss material from hopper 19 are introduced through gate 23 at a rate such that the particles cover planar bottom surface 18b' in a thin layer having a depth of typically one particle and at most a few times the average particle diameter. The particulate material then enters integrating chamber 18 through inlet opening 24. The center of depth of this thin layer along the length of integrating chamber 18 defines the plane of the particles in the chamber. The lower portion of the integrating chamber is situated so that the particulate material can be introduced at a controlled rate at one end of lower portion 18b, and is caused to move by the oscillatory motion of lower portion 18b along the longitudinal axis of the chamber in a direction generally transverse to the scanning beam. Lower portion 18b of the integrating chamber is positioned such that the second focal plane of the scan lens coincides with the plane of the particles. The laser beam is scanned across the lower portion of the integrating chamber approximately 5000 times per second. The depth of focus of the focused laser beam is typically several times greater than the depth of the particle layer, so that all the particles are illuminated with the same size laser beam. The intersection of the plane of the particles with the plane of rotation of rotating mirror 28 defines a line along which the focused scanning beam traverses. Any portion of the beam not absorbed by the contaminants in the particles being analyzed will be diffusely reflected by the particles, lower portion 18b of the integrating chamber or upper portion 18a of the chamber.

The particles to be examined are introduced from feed hopper 19 to lower portion 18b of the integrating chamber. The amplitude of oscillation of the feeder assembly is set to provide a stable flow of particles consistent with the input feed rate, which is determined by flow regulating gate 23. The particles flow through the integrating chamber and fall into receptacle 27 upon exit from the chamber. The separation control signal is generated as a result of the detection of contamination in the area of the integrating chamber illuminated by the scanning laser beam. Those particles identified as contaminated are collected separately by the separation subsystem.

On each scan, the scan detection circuit of photodetector assembly 40 generates a signal as the laser beam passes over it. This signal is used to start third down counter 100. Clock pulses from clock 92 cause third down counter 100 to count down from a software-controlled value. The software-controlled value is defined by the operator and is sent from CPU board 60 via VME interface section 78 to third input register 110 to generate a time delay. When third down counter 100 reaches a count of zero, it produces a signal at its output to initiate the automatic gain control sequence, which consists of three signals that occur after each scan detect signal. As noted above, the HOLD signal is the first signal in the automatic gain control sequence. The HOLD signal causes sample and hold amplifier 116 to acquire a sample of the signal from preamplifier module 46. The second signal in the automatic gain control sequence is the ADCONV signal, which causes the signal held by sample and hold amplifier 116 to be digitized. The third signal in the automatic gain control sequence is the DACREFRW signal, which causes the digital signal at its input to be converted to analog form by second D/A converter 138.

Automatic gain control section 90 compares the analog value to a high-voltage reference level. The high-voltage reference level is generated by second D/A converter 138. The high-voltage reference level is controlled by the operator via CPU board 60 and via VME interface section 78 and second D/A converter 138. The analog signal from first D/A converter 122 is compared to the high-voltage reference level from second D/A converter 138. The difference between the analog signal from first D/A converter 122 and the high-voltage reference level from second D/A converter 138 is integrated by integrator amplifier 126. Integrator amplifier 126 controls, via analog switch 127 and inverting amplifier 128, the high-voltage level sent to photodetector assembly 44, and thus controls the gain of assembly 44 to provide a constant output signal level therefrom.

The scan detection signal is also sent to first down counter 96. First down counters 96 is loaded in a manner similar to that previously described for loading third down counter 100. When the scan detect signal is generated, first down counter 96 begins counting down from its initial value until it reaches a count of zero. The initial value loaded into first down counter 96 is such that down counter 96 reaches its count of zero when the scanning laser beam has advanced to first edge 18$b''$ of lower portion 18$b$ of the integrating chamber. The initial value loaded into second down counter 98 is such that down counter 98 reaches its count of zero when the scanning laser beam has advanced to second edge 18$b'''$ of lower portion 18$b$ of the integrating chamber. The output of first down counter 96 sets flip-flop 94, and the output of second down counter 98 resets flip-flop 94 to generate the HBLANK signal, which controls the operation of second analog switch 132.

The signal generated by photodetector assembly 44 resulting from the scanning laser beam being scattered and/or absorbed by the particles is sent via buffer amplifier 114 to amplifier 118. The output signal from amplifier 118 is the difference between the output of first low-pass filter 124 and the output of first buffer amplifier 114. Second analog switch 132 is controlled so that the signal from amplifier 118 is further processed only during the time interval that the scanning laser beam is scanning planar surface 18$b'$ of lower portion 18$b$ of the integrating chamber.

The voltage level of the output signal from second analog switch 132, in the absence of contaminants, is nominally zero volts. When the laser beam scans across a contaminant which absorbs light, the voltage level of the signal from analog switch 132 increases. The amplitude of the increase in voltage corresponds to the size and optical absorption of the contaminant. In operation, comparators 88$a'$–88$e'$ and 88$a''$–88$e''$ are each provided with threshold voltage levels, the threshold voltage level of each comparator being higher than the threshold voltage level of the preceding comparator. Since each comparator 88$a'$–88$e'$ and 88$a''$–88$e''$ has a correspondingly higher threshold voltage level, it is thus possible to size-discriminate contaminants, based upon which comparators' output states (i.e., logic-High and logic-Low) change. Since comparators 88$a'$–88$e'$ receive the low-pass filtered signal from second low-pass filter 136, they are responsive only to larger contaminants such as discolored particles. It is also possible to determine the time duration of a signal which exceeds a given threshold level as an additional method to size discriminate contaminants.

If a contaminant causes an increase in voltage level that exceeds one of the threshold voltage levels of one of comparators 88$a'$–88$e'$ or 88$a''$–88$e''$, the comparator output changes from logic-Low to logic-High while the signal level is above the threshold voltage level. For small contaminant particles, this change in state may be very brief, typically less than a micro-second and possibly only a few nanoseconds in duration. The change in state of the comparators is captured by flip-flop 144, which enables fourth down counter 146. When fourth down counter 146 reaches a count of zero, it causes the count of accumulator counter 142 to increase by one. The delay of the number of HBLANK signals that must be counted reduces the possibility that a single contaminant will be counted more than once. The accumulated count of accumulator 142 is periodically read by CPU board 60 via VME interface section 78, stored in memory board 70 of the CPU board and displayed on terminal 62.

The software stored in CPU board 60 generates a file, which, after input from the user, contains user information such as product type and weight, as well as measured information such as elapsed time, contaminant counts from each event processor, and calculated values such as per unit weight of product examined. A data base of results is maintained on non-volatile memory board 70. A data base of files of control parameters files is also maintained on memory board 70. Control parameters include input values for fourth down counter 146 of each event processor 84$a'$–84$e'$ and 84$a''$–84$e''$ of event processor section 84, input values for third down counter 100 used for automatic gain control, input values for first and second down counters 96 and 98, respectively, used to control second analog switch 132 and input values for first D/A converter 122 and multiple input values for second D/A converter 138 and HVSEL status.

Figure 11:
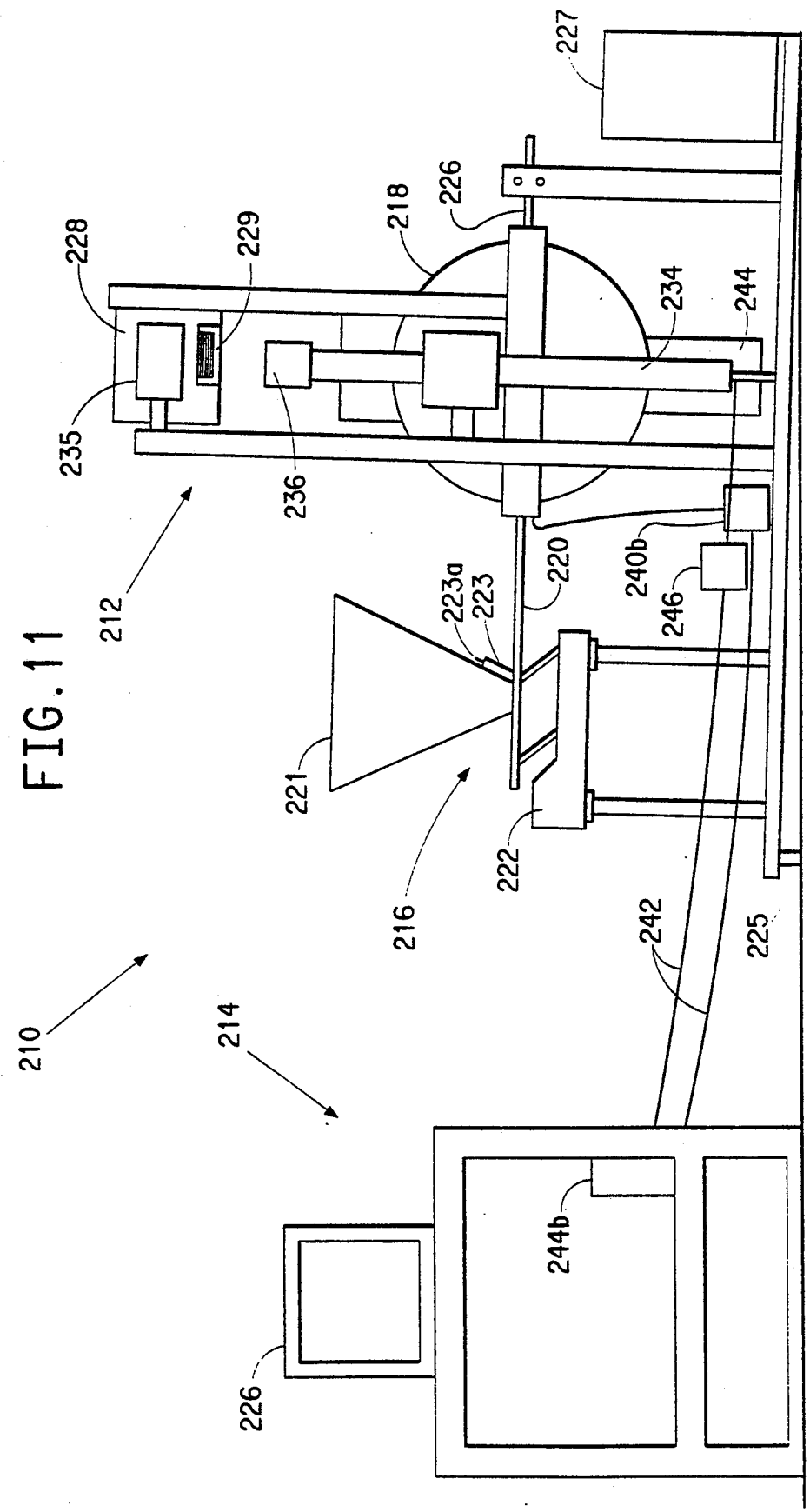
FIG. 11 is an elevational view of an apparatus for detecting contamination in particles of low optical-loss material according to a second embodiment of the present invention.

FIGS. 11–14 illustrate a second embodiment of the apparatus for optically detecting light-absorbing contamination in at least one particle of low optical-loss material of the present invention. The apparatus for optically detecting contamination in particles of low optical-loss material is shown generally at 210 in FIG. 11. Apparatus 210 comprises an optical subsystem shown generally at 212 and a computer subsystem shown generally at 214. Apparatus 210 comprises an optical integrating chamber 218 for containing the at least one particle. Optical integrating chamber 218 is part of optical subsystem 212. As shown in FIG. 11, integrating chamber 218 is substantially spherical in shape. Integrating chamber 218 comprises a generally hemispherical upper portion 218$a$ and a generally hemispherical lower portion 218$b$. In the second embodiment, upper portion 218$a$ comprises a stationary cover.

Integrating chamber 218 has a plurality of interior walls which are covered with a nearly lambertian, diffusely reflective, light-scattering material. A paint containing barium sulfate, such as White Reflective Coating, Part Number 6080, available from Eastman Kodak Company of Rochester, N.Y., has been found to be suitable for coating the interior walls of the integrating chamber of the second embodiment of the present invention.

Figure 12:
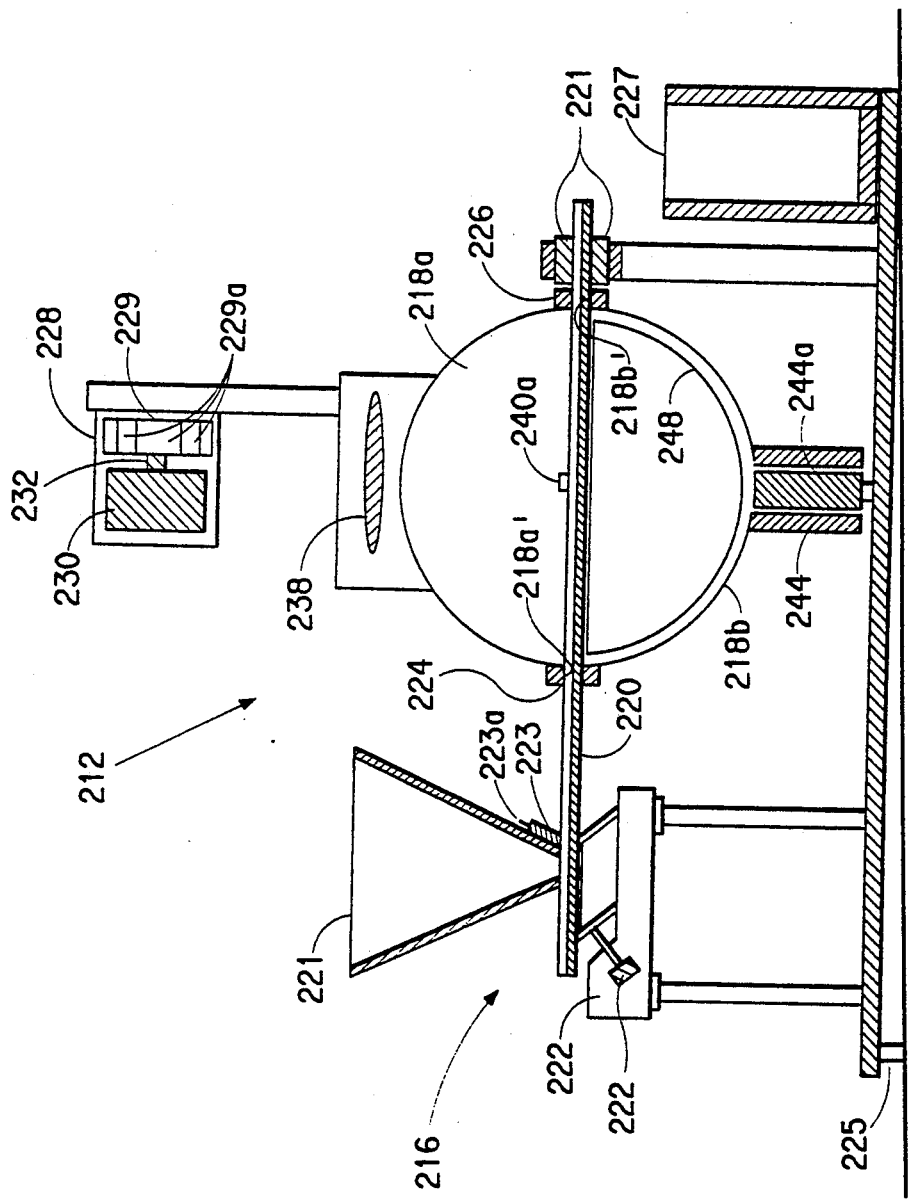
FIG. 12 is a partial cross-sectional view of the apparatus shown in FIG. 11 showing the optical subsystem of the present invention.
Figure 13:
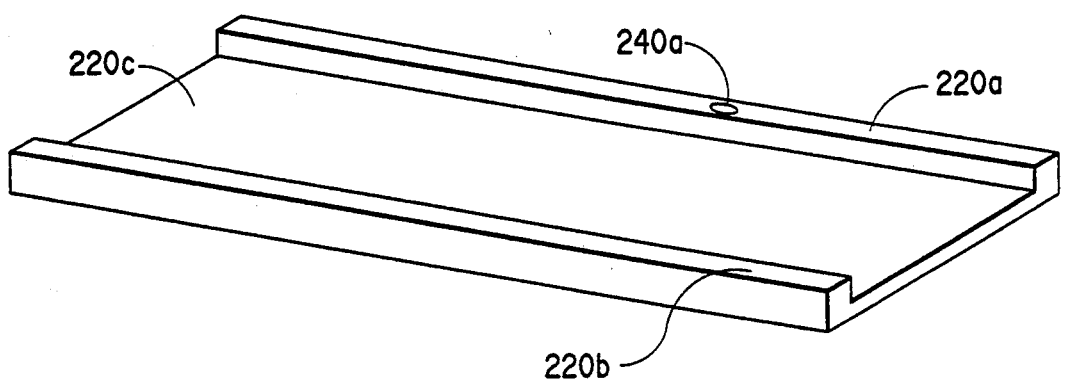
FIG. 13 is an enlarged, perspective view of the trough of the present invention as shown in FIGS. 11 and 12.

The apparatus according to the second embodiment of the present invention further comprises a transparent trough for containing and transporting the particles. As shown in FIGS. 11 and 12, a trough 220 for containing and transporting the particles extends through the center of integrating chamber 218 and is disposed between hemispherical upper portion 218a and hemispherical lower portion 218b. Trough 220 is elongated, has a longitudinal axis, (i.e., a plane of lateral symmetry) is generally symmetrical about its longitudinal axis and is adapted for oscillation therealong. As shown in FIG. 13, trough 220 includes a first upper peripheral edge 220a, a second upper peripheral edge 220b and a planar surface 220c on which the particles of material rest. In the embodiment as shown in FIGS. 11-14, the particles of low optical-loss material are disposed in the center of the integrating chamber rather than on the bottom thereof as in the embodiment of FIGS. 1-10. A transparent trough is mounted in place of the metal trough of the vibratory feeder of Model 20A from Eriez Magnetics as used in the first embodiment. The trough is made from a block of polymethyl methacrylate, sold by Du Pont under the trademark "LUCITE", which is optically polished and thus made transparent.

In accordance with the second embodiment of the present invention, trough 220 includes a damper 220d disposed at one longitudinal end thereof to reduce the vertical vibration of the trough and to keep the particles of material from bouncing vertically. Damper 220d is typically comprised of C-3000 series energy absorbing foam, sold under the trademark "ISODAMP" by EAR Specialty TM Composites Division of Cabot Safety Corporation of Indianapolis, Ind.

The apparatus of the second embodiment of the present invention also comprises a vibratory feeder assembly shown generally at 216 in FIGS. 11 and 12 for feeding particles to the trough at a controlled rate. Vibratory feeder assembly 216 comprises a hopper 221 and a flow regulating gate 223. Vibratory feeder assembly 216 also includes a motor 222, which drives trough 220 in an oscillatory motion. The motor may be a reciprocating piston motor. When the motor piston reciprocates, trough 220 moves in an oscillatory fashion, primarily along the longitudinal axis thereof, but with a small component of vertical motion. The motor and thus the trough typically oscillate with an amplitude of about one millimeter, at a frequency of about sixty Hertz. The vibratory feeder assembly may be positioned such that it is level or is inclined along its longitudinal axis. Vibratory feeder assembly 216 is adjustable by adjusting a leg 225 as shown in FIGS. 11 and 12, which allows the angle to be varied up to about 10° for a lower feed rate or lower for a higher feed rate. The particles of material are distributed along planar surface 220c and are transported through the trough due to the oscillatory motion thereof and due to gravity. A suitable feeder assembly according to the second embodiment of the present invention may be made by modifying commercially available vibratory feeder assembly, Model 20A from Eriez Magnetics of Erie, Pa., as used in the first embodiment.

Upper portion 218a includes a lower peripheral edge 218a', and lower portion includes an upper peripheral edge 218b' as shown in FIG. 12. An inlet opening 224 and an outlet opening 226 are formed at the longitudinal ends of the upper and lower portions by the planar surface of lower portion 218b and lower peripheral edge 218a' of upper portion 218a so that the particles pass unobstructed through the chamber. Trough 220 extends through openings 224 and 226 as shown in FIGS. 11 and 12.

Hopper 221 is positioned a predetermined distance above trough 220 between motor 222a and inlet opening 224. The outlet of hopper 221 is slightly narrower than the width of planar surface 220c of trough 220. The edge of the hopper outlet adjacent motor 222 is disposed at a distance, typically one-half the size of an average particle, from the planar surface of trough 220 to prevent the particles from escaping. The dimension of the width of the hopper outlet is typically about one-quarter to one-half the hopper outlet width. Such a configuration creates a reservoir for the particles at the hopper outlet to insure uniform coverage of the planar surface of the trough. The particles of material enter the integrating chamber through inlet opening 224 and exit the integrating chamber through outlet opening 226 to a receptacle 227.

Flow-regulating gate 223 regulates the flow of particles at the entrance to the trough. Flow-regulating gate 223 is disposed above planar surface 220c of trough 220 on the edges of the outlet of hopper 221 adjacent inlet opening 224. Flow-regulating gate 223 is manually adjustable by adjusting knob 223a. Flow-regulating gate 223 ensures that a uniform layer of particles of a controlled thickness is spread along the planar surface of the trough.

Further in accordance with the second embodiment of the present invention, the apparatus for optically detecting light-absorbing contamination in particles of low optical-loss material also comprises a laser 234 as shown in FIGS. 11 and 12 for emitting a laser beam which illuminates the particles. The light from the laser beam is either reflected from or transmitted through the particles, which are made of low optical-loss material. The laser used in the second embodiment of the present invention is a commercially available, off-the-shelf item, such as the laser used in the first embodiment. However, different types of lasers may be used to detect contamination, depending on the material being inspected. Laser 234 preferably includes a telescopic lens assembly 236, which comprises a collimating lens and a beam expander, for expanding and collimating the laser beam. A suitable telescopic lens assembly for use with the second embodiment of the present invention, such as Model 09LBM011 from Melles Griot, as used in the first embodiment, is used to expand and collimate the laser beam to a diameter of about three millimeters.

As embodied herein, the apparatus for optically detecting light-absorbing contamination in accordance with the second embodiment also comprises a scanning assembly mounted in optical alignment with the laser for reflecting the laser beam and for causing the laser beam to scan the particle in the optical integrating chamber. A scanning assembly is shown generally at 228 in FIGS. 11 and 12. Scanning assembly 228 includes a rotating mirror 29 mounted adjacent the integrating chamber, a motor 230 and a shaft 232. Mirror 229 has at least one reflective face 229a disposed about the circumference thereof and an axis of rotation substantially parallel to the longitudinal axis (i.e., the plane of lateral symmetry) of trough 220. Mirror 229 is rotatably supported on shaft 232 and is rotatable about its axis of rotation by the motor. The plane of rotation of the rotating mirror is substantially orthogonal to planar surface 220c of trough 220, but may be inclined from the orthogonal, if desired. A beam-folding mirror 235 is provided in the path of laser 234 to direct the laser beam to faces 229a of rotating mirror 229. Laser 234 is mounted in the plane of the rotation of rotating mirror 229 such that the laser beam reflects from the reflective faces of the rotating mirror and scans in a fan scan. The fan scan is oriented in a direction substantially perpendicular to planar surface 220c and lies in the plane of rotation of the rotating mirror. The scanning assembly used in the present invention is a commercially available, off-the-shelf item, such as that used with the first embodiment. Alternatively, in the second embodiment of the present invention, the scanning assembly could be a galvanometer-driven, rotating mirror, a resonant torsional scanner, a holographic scanner or an accousto-optic deflector.

As embodied herein, the apparatus of the second embodiment of the present invention also comprises a focusing assembly mounted in optical alignment with the laser for focusing the scanning laser beam onto the particles in the chamber, the focusing assembly operating in conjunction with the scanning assembly so that light from the laser beam is reflected from the particles and is repeatedly scattered onto the interior walls of the integrating chamber. As shown in FIG. 12, apparatus 210 comprises a focusing assembly including a scan lens 238. Scan lens 238 is mounted between integrating chamber 218 and rotating mirror 229. Scan lens 238 converts the fan scan into a telecentric scan and focuses the scanning laser beam onto the particles in trough 220. Scan lens 38 operates in conjunction with rotating mirror 229 so that light from the laser beam is transmitted through or reflected from the particles and is repeatedly scattered onto the interior walls of the integrating chamber. The vertical position of scan lens 238 is adjustable relative to trough 220 in order to accurately focus the beam on the particles. Thus, the laser beam stays uniformly focused across the entire width of planar surface 220c of trough 220. A scan lens suitable for use with the second embodiment of the present invention is a custom hyperbolic lens having an eight-inch diameter and an eight-inch focal length, available from Applied Products, Inc. of Horsham, Pa. Alternatively, the focusing assembly may comprise a telescopic lens assembly mounted between the laser and the scanning assembly as described with respect to the first embodiment.

Scan lens 238 is mounted with respect to rotating mirror 229 so that the scanning collimated beam passes through the lens along the central chord of the lens. Since the laser beam is collimated as it passes the first focal plane of the lens, the lens causes the beam to focus at the second focal plane of the lens. The apparent origin point of the scanning beam is at the first focal plane of the lens, and thus the lens transforms the fan scan into a telecentric scan. The telecentric scan maintains a constant incidence angle of the scanning laser beam on the particles to ensure that the sensitivity to contaminants is uniform across the width of the lower portion. The laser, scanning assembly, the beam folding mirror and the scan lens of the second embodiment are enclosed in a suitable metal enclosure (not shown) to prevent external light from entering the apparatus and to keep dirt out of the system.

Figure 14:
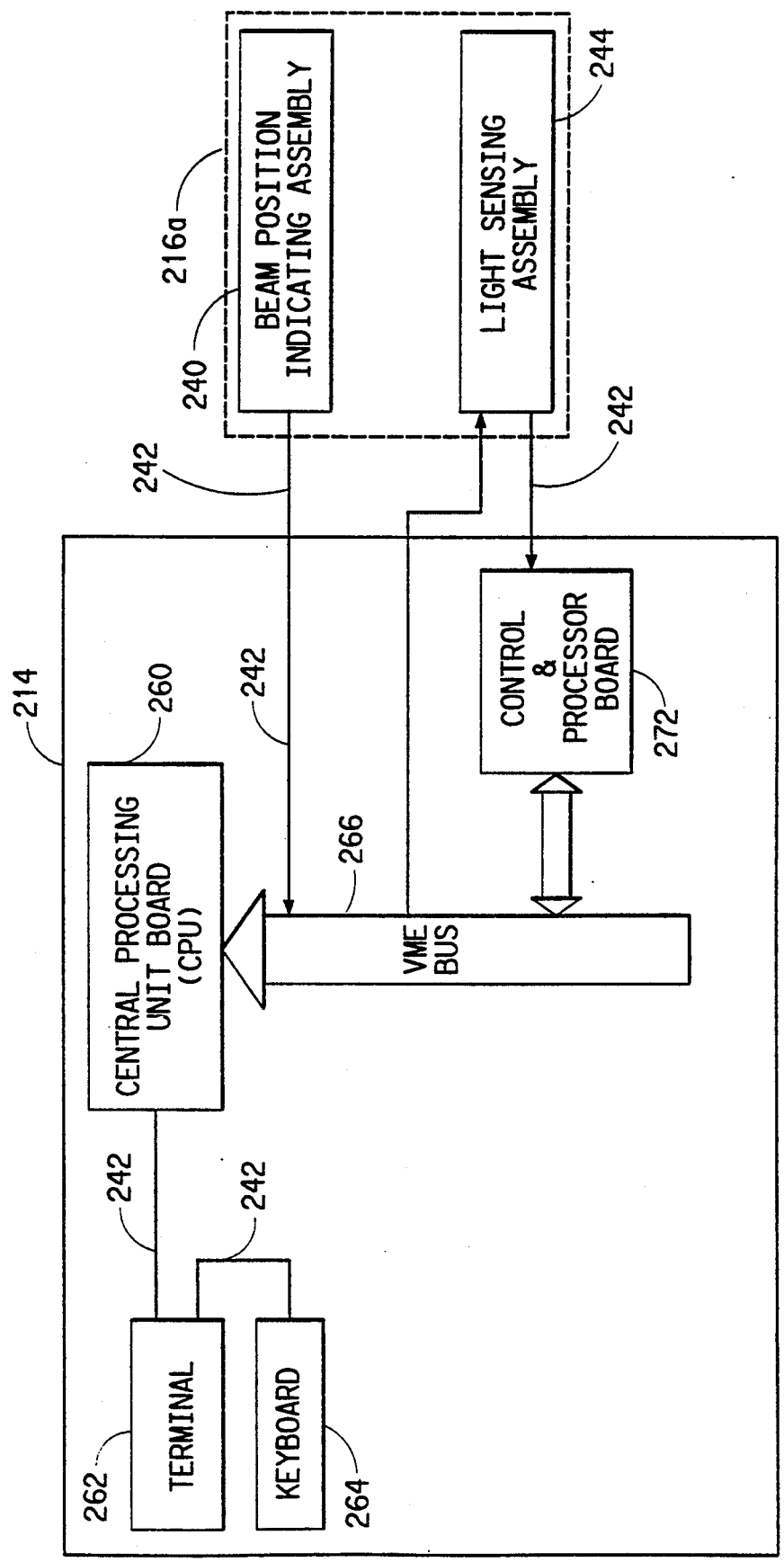
FIG. 14 is a system block diagram of the components of the computer subsystem of the apparatus according to the second embodiment of the present invention.

The apparatus of the second embodiment of the present invention also includes a laser beam position indicating assembly mounted in a fixed relationship to the scanning assembly for detecting when the scanning laser beam reaches a predetermined point and for generating a scan detection signal in response thereto. As shown in FIG. 14, apparatus 210 comprises a laser beam position indicating assembly, which is preferably a photodetector, or start of scan detection, assembly 240. Alternatively, the laser beam position indicating assembly may comprise a magnetic detector for detecting the angular position of the scanning assembly. Photodetector assembly 240 is mounted inside integrating chamber 218 on first upper peripheral edge 220a of trough 220 as shown in FIG. 13. Photodetector assembly 240 includes a photodetector 240a as shown in FIGS. 12 and 13 and a scan detection circuit 240b as shown in FIG. 11. Photodetector 240a of photodetector assembly 240 is preferably a photodiode which is split into a first and second portion. A suitable split photodiode for use as the photodetector of the laser beam position indicating assembly of the second embodiment of the present invention is the same as that used in the first embodiment.

The apparatus for optically detecting light-absorbing contamination in accordance with the second embodiment of the present invention also comprises a light sensing assembly for generating an intensity signal indicative of the intensity of the repeatedly scattered light, wherein a decrease in the intensity of the repeatedly scattered light is a function of the presence of light-absorbing contamination in the material. Preferably, in the second embodiment, the light sensing assembly comprises a photodetector assembly 244 as shown in FIG. 14 mounted adjacent the integrating chamber for receiving light repeatedly scattered in the chamber. In this context, adjacent may mean either in, on or near. Photodetector assembly 244 is part of optical subsystem 212. Photodetector assembly 244 is mounted on the outside of lower portion 218b of integrating chamber 218, below trough 220. Alternatively, photodetector assembly 244 may be mounted on upper hemispherical portion 218a of integrating chamber 218. Photodetector assembly 244 of the second embodiment preferably includes a photomultiplier tube 244a as shown in FIGS. 12 and 13 and a high-voltage power supply 244b as shown in FIG. 11 for the photomultiplier tube. High-voltage power supply 244b resides in computer subsystem 214 as shown in FIG. 11. A suitable photomultiplier tube for use with the second embodiment of the present invention is model 8654 from Burle Industries of Lancaster, Pa. as in the first embodiment. A high voltage power supply suitable for use with the second embodiment of the present invention is Model PMT-10C/N from Bertan Associates, Inc. of Hicksville, N.Y. Although a photomultiplier tube is used with the second embodiment of the present invention, alternatively, the light sensing assembly may comprise another type of photodetector, such as a photodiode, or a vacuum photodiode.

Photodetector assembly 244 receives light repeatedly scattered from the interior walls of the integrating chamber and generates an intensity signal. The apparatus of the second embodiment of the present invention operates according to the same optical principles as described above with respect to the first embodiment.

Thus, the intensity signal generated by the photodetector assembly of the light sensing assembly is indicative of intensity of the light repeatedly scattered from the interior walls of the integrating chamber.

The apparatus of the second embodiment of the present invention further includes a signal processing assembly connected to the photodetector assembly of the light sensing assembly for amplifying and filtering the intensity signal. The signal processing assembly of the second embodiment comprises a preamplifier module 246 as shown in FIG. 11. Preamplifier module 246 amplifies the intensity signal generated by photodetector assembly 244 and converts it into a voltage which is transmitted to computer subsystem 214.

The cables for connecting the components of optical subsystem 212 to computer subsystem 214, and the components of computer subsystem 214 to each other, are all designated by reference numeral 242. The scan detection signal generated by the scan detection circuit of photodetector assembly 240 and the intensity signal generated by photodetector assembly 244 are transmitted via cables 242 to computer subsystem 214 as shown in FIGS. 11 and 14.

The apparatus of the second embodiment of the present invention also comprises a baffle 248 mounted inside the integrating chamber to ensure that only repeatedly scattered light is incident on the photodetector assembly of the light sensing assembly. As shown in FIG. 12, baffle 248 is mounted in lower portion 218b of integrating chamber 218. The surfaces of the light baffle are coated with the same White Reflective Coating, Part Number 6080, available from Eastman Kodak Company, and thus have the same optical properties (i.e., nearly lambertian, diffusely reflective and light-scattering) as the interior walls of upper portion 218a and lower portion 218b of the integrating chamber. The baffle operates in accordance with the optical principles described with respect to the first embodiment. FIG. 14 is a simplified block diagram of computer subsystem 214 used in accordance with the second embodiment of the present invention. Referring to FIG. 14, computer subsystem 214 includes a Central Processor Unit (CPU) board 260 for controlling the computer subsystem. Specifically, the CPU board generates control and data signals in response to a compiled computer program stored in a Read Only Memory (ROM), which may be located on the CPU board. Alternatively, the ROM may be on a separate support board. A CPU board suitable for use with the present invention is Model SYS68K/CPU-29 from Force Computers, Inc. of Los Gatos, Calif.

CPU board 260 is connected by cable 242 to a terminal 262, which includes a keyboard 264. Terminal 262 allows the user to control operation of the apparatus by interacting with CPU board 260. A terminal used with the computer subsystem of the second embodiment of the present invention is typically Model 330 from Digital Equipment Corporation of Maynard, Mass., which includes a video monitor and a keyboard. CPU board 260 is connected to the rest of the computer subsystem via a VME bus 266. VME bus 266 transmits the control and data signals generated by CPU board 260 to other boards in computer subsystem 214. VME bus 266 is connected to beam position indicating assembly 240 and light sensing assembly 244 as shown in FIG. 14.

The apparatus in accordance with the second embodiment of the present invention further includes a signal processing assembly connected to the photodetector assembly of the light sensing assembly for amplifying and filtering the intensity signal. The signal processing assembly comprises a control and processor board 272. Control and processor board 272 is connected to CPU board 260 via VME bus 266. Control and processor board 272 is also connected by cable 242 to photodetector assembly 244 for receiving, amplifying and filtering the intensity signal generated thereby.

The rest of the computer subsystem of the second embodiment of the present invention is substantially the same as that shown and described with respect to the first embodiment, and thus, for simplicity sake, is not shown or illustrated again. However, control and processor board 272 as shown in FIG. 14 does not generate the BUF PMT, HSYNC, VSYNC and PXL CLK signals as shown in FIG. 5, and there is no separation control circuit in the second embodiment as in the first embodiment as shown in FIGS. 4 and 5. The rest of computer subsystem 214 of the second embodiment is substantially the same as that described with reference to FIGS. 6-10 of the first embodiment of the present invention. The operation of the apparatus of the second embodiment is substantially the same as that described for the first embodiment, except that, in addition to the differences noted above, the particles are moved through the integrating chamber by the oscillation of the transparent trough, rather than by the oscillation of the lower portion of the integrating chamber as in the first embodiment.

Figure 15:
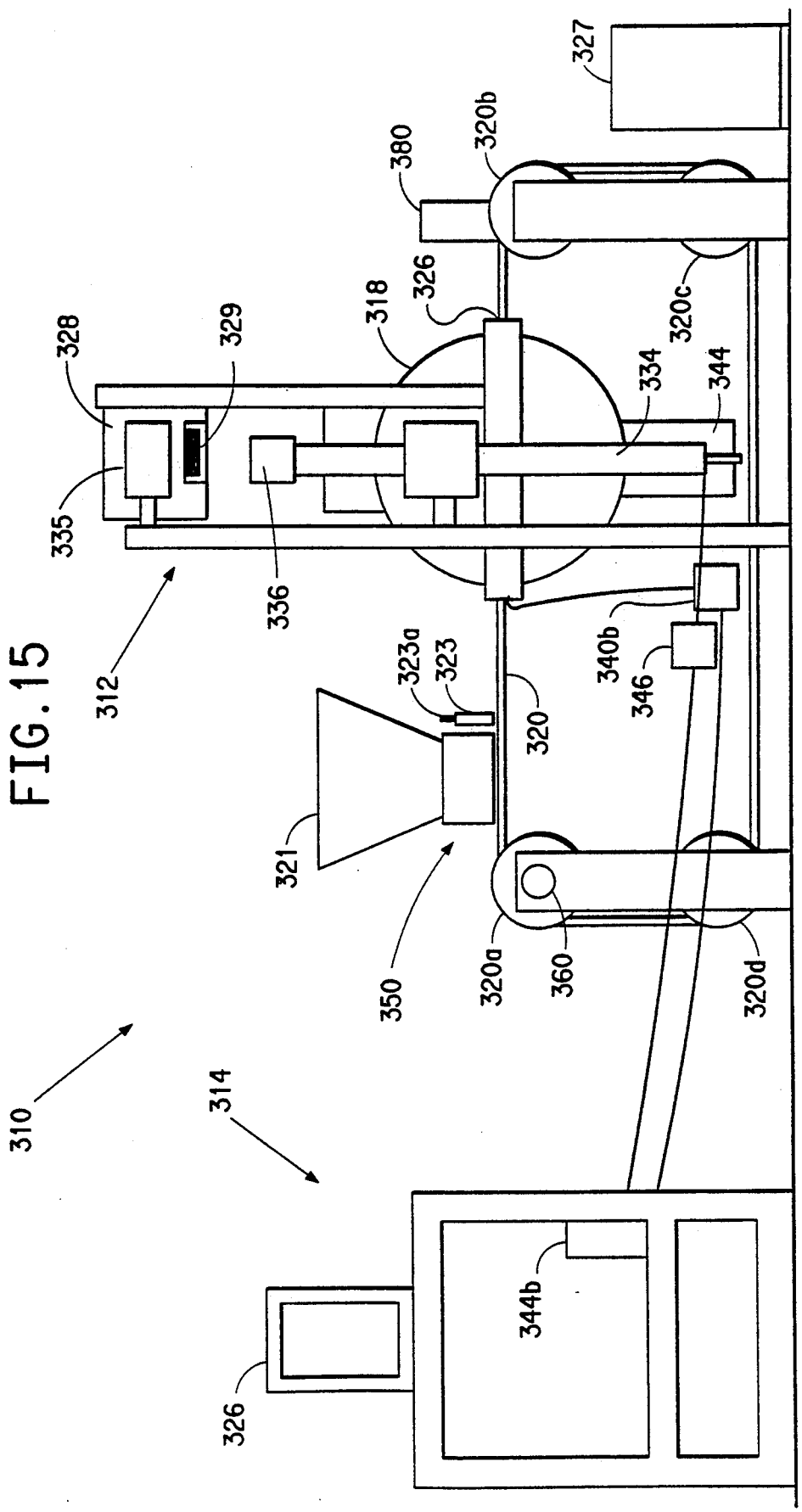
FIG. 15 is an elevational view of an apparatus for detecting contamination in particles of low optical-loss material according to a third embodiment of the present invention which employs a transparent belt.

A third embodiment of the present invention is shown in FIGS. 15-18. An apparatus for optically detecting contamination in at least one particle of low optical-loss material in accordance with the third embodiment is shown generally at 310 in FIG. 15 Apparatus 310 comprises an optical subsystem shown generally at 312 and a computer subsystem shown generally at 314 in FIG. 15. Apparatus 310 also comprises an optical integrating chamber 318 for containing the at least one particle. Optical integrating chamber 318 is part of optical subsystem 312. As shown in FIG. 15, integrating chamber 318 is substantially spherical in shape. Integrating chamber 318 comprises a generally hemispherical upper portion 318a and a generally hemispherical lower portion 318b. In the third embodiment, upper portion 318a comprises a stationary cover. Integrating chamber 318 has a plurality of interior walls which are covered with a nearly lambertian, diffusely reflective, light-scattering material. A paint containing barium sulfate, such as that used for the integrating chamber of the second embodiment is suitable for coating the interior walls of the integrating chamber of the third embodiment of the present invention.

Figure 16:
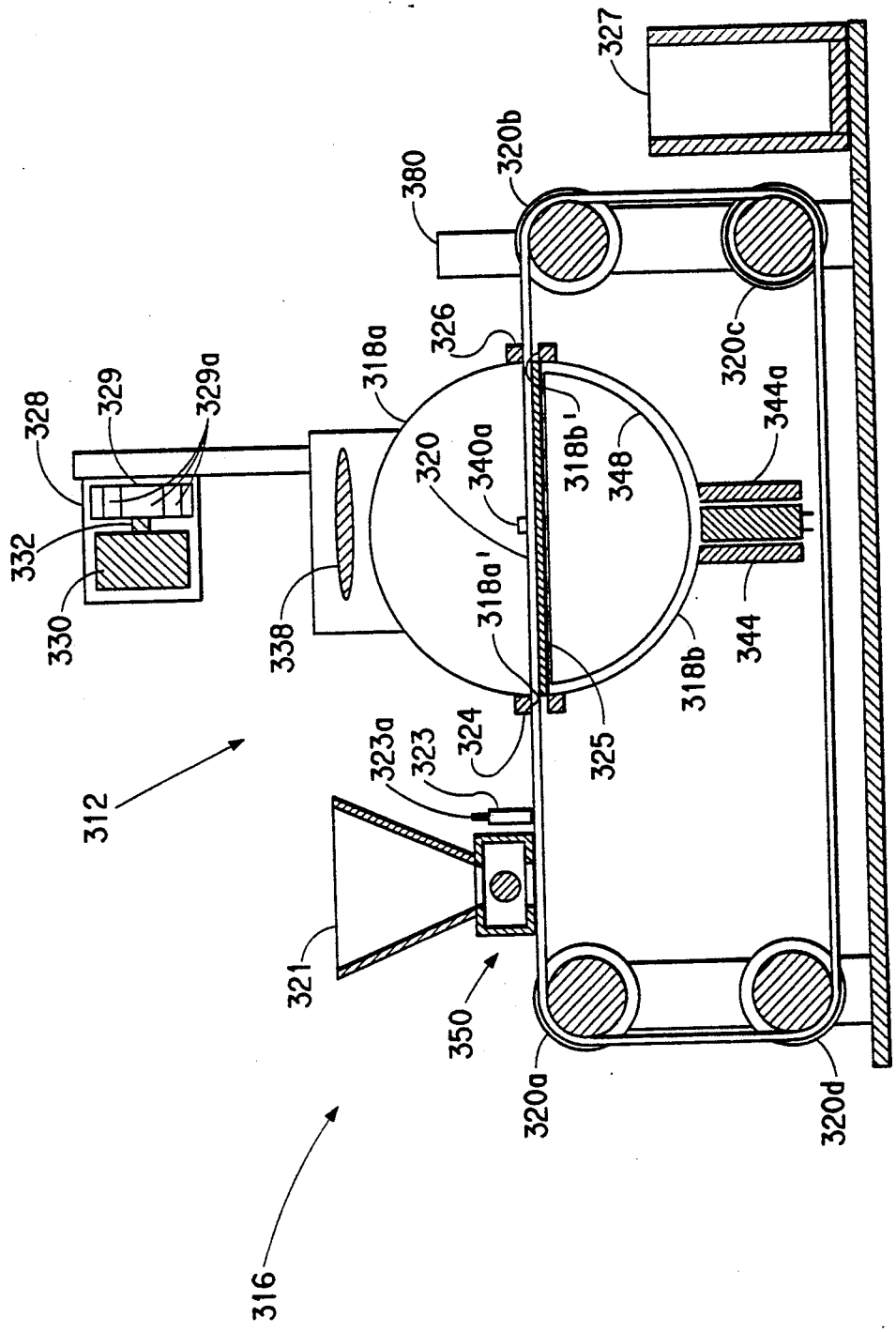
FIG. 16 is a partial cross-sectional view of the apparatus shown in FIG. 15 showing the optical subsystem of the present invention.
Figure 17:
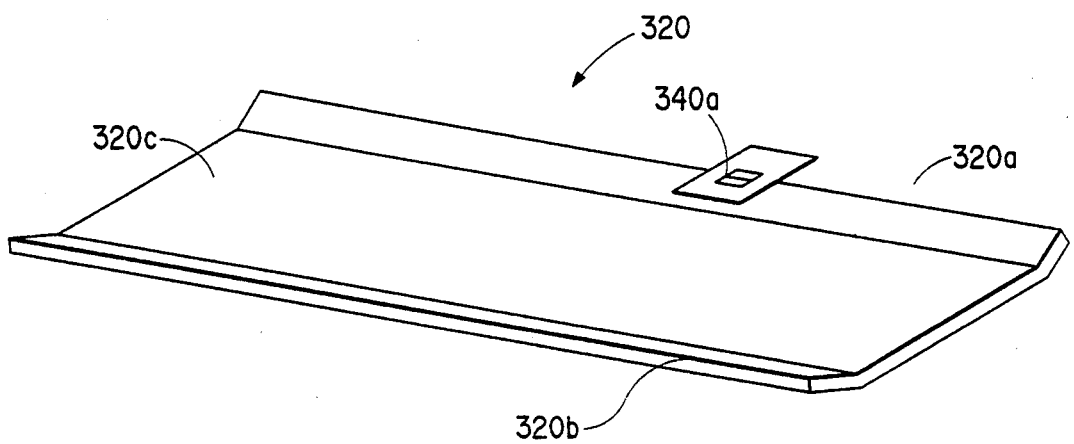
FIG. 17 is an enlarged, perspective view of the belt of the present invention as shown in FIGS. 15 and 16.

The apparatus according to the third embodiment of the present invention further comprises a transparent belt 320 as shown in FIGS. 15-17 for holding and transporting the particles. Belt 320 is disposed between the upper portion and the lower portion of the integrating chamber and is supported on a plurality of pulleys 320a-d and a transparent support 325 as shown in FIG. 16. The belt has a longitudinal axis and is adapted for movement therealong. The belt may be positioned such that it is level or is inclined along its longitudinal axis. As shown in FIG. 17, belt 320 includes a planar surface 320c. The belt may be made of transparent polyethylene terephthalate film, sold by Du Pont under the trademark "MYLAR". In the third embodiment, higher feed rates through the integrating chamber than those of the first and second embodiments may be attained while maintaining the particles of material flat on the belt. Since the particles are stationary relative to the belt, the position of contaminants can be more accurately determined and contaminants subsequently removed from the particle stream exiting the belt with minimum loss of acceptable particles. A belt positioning assembly, such as a rotary encoder, may be used to generate a belt motion signal.

The apparatus of the third embodiment of the present invention also comprises a screw feeder assembly for feeding particles to the belt at a controlled rate. A screw feeder assembly is shown generally at 350 in FIGS. 15 and 16. Screw feeder assembly 350 comprises a hopper 321, an optional flow regulating gate 323 and a motor (not shown). Feeder assembly 350 is adjustable by the speed of its motor to feed particles onto the belt at a controlled rate. The particles of material are distributed along planar surface 320c and are transported through the integrating chamber due to the movement of the belt. A commercially available screw feeder assembly, such as Model 600, dry material feeder from Accurate, Inc. of Whitewater, Wis., is suitable for use with the apparatus according to the third embodiment of the present invention.

Upper portion 318a of integrating chamber 318 includes a lower peripheral edge 318a' and lower portion 318b includes an upper peripheral edge 318b'. An inlet opening 324 and an outlet opening 326 are formed at the longitudinal ends of the upper and lower portions by the planar surface of lower portion 318b and lower peripheral edge 318b' of upper portion 318a so that the particles pass unobstructed through the chamber. Belt 320 extends through openings 324 and 326 as shown in FIGS. 15 and 16. Screw feeder assembly 350 is positioned a predetermined distance above belt 320 ahead of inlet opening 324. The outlet of feeder assembly 350 is equal to or slightly narrower than the width of the planar surface of belt 320. The outlet opening of screw feeder assembly 350 is a slot extending across planar surface 320c of belt 320.

Optional flow-regulating gate 323 regulates the flow of particles at the entrance to the belt. Flow-regulating gate 323 is disposed above planar surface 320c of belt 320 between screw feeder assembly 350 and inlet opening 324. Flow-regulating gate 323 is manually adjustable by adjusting knob 323a. Flow-regulating gate 323 ensures that a uniform layer of particles of a controlled thickness is spread along the planar surface of the belt. The particles of material enter the integrating chamber through inlet opening 324 and exit the integrating chamber through outlet opening 326 to a receptacle 327.

Further in accordance with the third embodiment of the present invention, the apparatus for optically detecting light-absorbing contamination in at least one particle of low optical-loss material also comprises a laser 334 for emitting a laser beam to illuminate the particle as shown in FIGS. 15 and 16. The light from the laser beam is either reflected from or transmitted through the particles, which are made of low optical-loss material. The laser used in the third embodiment of the present invention is a commercially available, off-the-shelf item, such as that used with the first two embodiments. However, different types of lasers may be used to detect contamination, depending on the material being inspected. Laser 334 preferably includes a telescopic lens assembly 336, which comprises a collimating lens and a beam expander, for collimating and expanding the laser beam. The telescopic lens assembly used with the first two embodiments is suitable for use with the third embodiment of the present invention to expand and collimate the laser beam to a diameter of about three millimeters.

As embodied herein, the apparatus for optically detecting light-absorbing contamination in accordance with the third embodiment also comprises a scanning assembly shown at 328 in FIGS. 15 and 16 mounted in optical alignment with the laser for reflecting the laser beam and for causing the laser beam to scan the particles in the optical integrating chamber. Scanning assembly 328 includes a rotating mirror 329, a motor 330 and a shaft 332. Mirror 329 has at least one reflective face 329a disposed about the circumference thereof and an axis of rotation substantially parallel to the longitudinal axis of belt 320. Mirror 329 is rotatably supported on shaft 332 and is rotatable about its axis of rotation by the motor. The plane of rotation of the rotating mirror is substantially orthogonal to planar surface 320c of belt 320, but may be inclined from the orthogonal, if desired. A beam-folding mirror 335 as shown in FIG. 15 is provided in the path of laser 334 to direct the laser beam to faces 329a of rotating mirror 329. Laser 334 is mounted in the plane of the rotation of rotating mirror 329 such that the laser beam reflects from the reflective faces of the rotating mirror and scans in a fan scan. The fan scan is oriented in a direction substantially perpendicular to planar surface 320c and lies in the plane of rotation of the rotating mirror. The scanning assembly used in the present invention is a commercially available, off-the-shelf item, such as that used with the first two embodiments. Alternatively, in the third embodiment of the present invention, the scanning assembly could be a galvanometer-driven, rotating mirror, a resonant torsional scanner, a holographic scanner or an accousto-optic deflector.

As embodied herein, the apparatus of the third embodiment of the present invention also comprises a focusing assembly mounted in optical alignment with the laser for focusing the scanning laser beam onto the particles in the chamber, the focusing assembly operating in conjunction with the scanning assembly so that light from the laser beam is transmitted through or reflected from the particles and is repeatedly scattered onto the interior walls of the integrating chamber. As shown in FIG. 15, apparatus 310 comprises a focusing assembly including a scan lens 338. Scan lens 338 is part of optical subsystem 312. Scan lens 338 is mounted between integrating chamber 318 and rotating mirror 329. Scan lens 338 converts the fan scan into a telecentric scan and focuses the scanning laser beam onto the particles on belt 320. Scan lens 338 operates in conjunction with rotating mirror 329 so that light from the laser beam is reflected from the particles and is repeatedly scattered onto the interior walls of the integrating chamber. The vertical position of scan lens 338 is adjustable relative to belt 320 in order to accurately focus the beam on the particles. Thus, the laser beam stays uniformly focused across the entire width of planar surface 320c of belt 320. A scan lens suitable for use with the third embodiment of the present invention is a custom hyperbolic lens having an eight-inch diameter and an eight-inch focal length, available from Applied Products, Inc. of Horsham, Pa. Alternatively, the focusing assembly may comprise a telescopic lens assembly mounted between the laser and the scanning assembly as described with respect to the first embodiment.

Scan lens 338 is mounted with respect to rotating mirror 329 so that the scanning collimated beam passes through the lens along the central chord of the lens. Since the laser beam is collimated as it passes the first focal plane of the lens, the lens causes the beam to focus at the second focal plane of the lens. The apparent origin point of the scanning beam is at the first focal plane of the lens, and thus the lens transforms the fan scan into a telecentric scan. The telecentric scan maintains a constant incidence angle of the scanning laser beam on the particles to ensure that the sensitivity to contaminants is uniform across the width of the lower portion. The laser, the scanning assembly, the beam folding mirror and the scan lens of the third embodiment are enclosed in a suitable metal enclosure (not shown) to prevent external light from entering the apparatus and to keep dirt out of the system.

Figure 18:
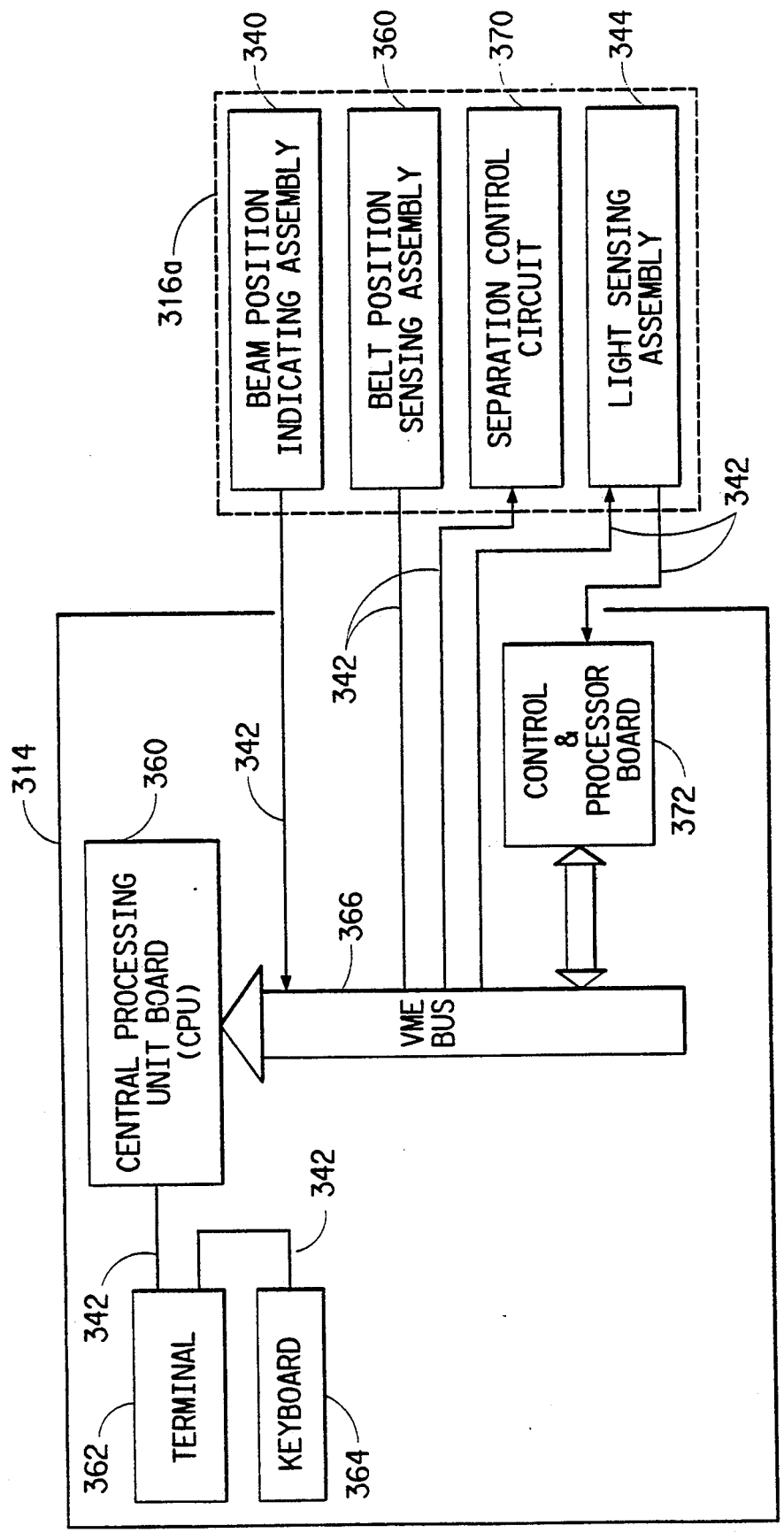
FIG. 18 is a system block diagram of the components of the computer subsystem of the apparatus according to the third embodiment of the present invention.

The apparatus of the third embodiment of the present invention also includes a laser beam position indicating assembly mounted in a fixed relationship to the scanning assembly for detecting when the scanning laser beam reaches a predetermined point and for generating a scan detection signal in response thereto. Preferably, the laser beam position indicating assembly comprises a photodetector, or start of scan detection, assembly 340 as shown in FIG. 18. Assembly 340 is part of optical subsystem 312. Alternatively, the laser beam position indicating assembly may comprise a magnetic detector for detecting the angular position of the scanning assembly. Such a detector may sense the position of the rotating mirror by sensing the passage of magnetic indicia thereon. Photodetector assembly 340 is mounted inside integrating chamber 318 as shown in FIG. 17. Photodetector assembly 340 includes a photodetector 340a as shown in FIGS. 16 and 17 and a scan detection circuit 340b as shown in FIG. 15. The photodetector of photodetector assembly 340 is preferably a photodiode which is split into a first and second portion. A suitable split photodiode for use as the photodetector of the laser beam position indicating assembly of the third embodiment of the present invention is a split photodiode such as that used with the first two embodiments.

The apparatus for optically detecting light-absorbing contamination in accordance with the third embodiment of the present invention also comprises a light sensing assembly for generating an intensity signal indicative of the intensity of the repeatedly scattered light, wherein a decrease in the intensity of the repeatedly scattered light is a function of the presence of light-absorbing contamination in the material. Preferably, in the third embodiment, as in the above embodiments, the light sensing assembly comprises a photodetector assembly mounted adjacent the integrating chamber for receiving light repeatedly scattered in the chamber. In this context, adjacent may mean either in, on or near. As shown in FIG. 15, apparatus 310 comprises a photodetector assembly 344. Photodetector assembly 344 is part of optical subsystem 312. Photodetector assembly 344 is mounted on the outside of lower portion 318b of integrating chamber 318, below belt 320. Alternatively, photodetector assembly 344 may be mounted on upper hemispherical portion 318a of integrating chamber 318. Photodetector assembly typically includes a photomultiplier tube 344a and a high-voltage power supply 344b for the photomultiplier tube. High-voltage power supply 344b resides in computer subsystem 314 as shown in FIG. 15. A suitable photomultiplier tube for use with the third embodiment of the present invention is model 8654 from Burle Industries of Lancaster, Pa. as in the first embodiment. A high voltage power supply suitable for use with the third embodiment of the present invention is Model PMT-10C/N from Bertan Associates, Inc. of Hicksville, N.Y. Although a photomultiplier tube is used with the third embodiment of the present invention, alternatively, the light sensing assembly may comprise another type of photodetector, such as a photodiode, or a vacuum photodiode. Photodetector assembly 344 receives light repeatedly scattered from the interior walls of the integrating chamber and generates an intensity signal. The apparatus of the third embodiment of the present invention operates according to the same optical principles as described above with respect to the first two embodiments, so that the intensity generated by photodetector assembly 344 is indicative of the intensity of the light repeatedly scattered from the interior walls of the integrating chamber.

The apparatus of the third embodiment of the present invention further includes a signal processing assembly connected to the photodetector assembly of the light sensing assembly for amplifying and filtering the intensity signal. The signal processing assembly of the second embodiment comprises a preamplifier module 346 as shown in FIG. 15. Preamplifier module 346 amplifies the intensity signal generated by photodetector assembly 344 and converts it to a voltage, which is transmitted to computer subsystem 214.

The cables for connecting the components of optical subsystem 312 to computer subsystem 314, and the components of computer subsystem 314 to each other, are all designated by reference numeral 342. The scan detection signal generated by the scan detection circuit of photodetector assembly 340 and the signal generated by photodetector assembly 344 are transmitted via cables 342 to computer subsystem 314 as shown in FIG. 18.

The apparatus of the third embodiment of the present invention also comprise a baffle 348 mounted inside the integrating chamber to ensure that only repeatedly scattered light is incident on the photodetector assembly of the light sensing assembly. Baffle 348 is mounted in lower portion 318b of integrating chamber 318 as shown in FIG. 16. Baffle 348 ensures that only light which has been repeatedly scattered can reach photodetector assembly 344. The surfaces of the light baffle are coated with the same white reflective coating as that used to coat the interior walls of the integrating chamber of this embodiment and as that used in the second embodiment. The optical properties of the surfaces are thus the same as those described above with respect to the first two embodiments.

FIG. 18 is a simplified block diagram of a computer subsystem shown generally at 314 in FIG. 15 and used in accordance with the second embodiment of the present invention. Referring to FIG. 18, computer subsystem 314 includes a Central Processor Unit (CPU) board 360 for controlling the computer subsystem. Specifically, the CPU board generates control and data signals in response to a compiled computer program stored in a Read Only Memory (ROM), which may be located on the CPU board. Alternatively, the ROM may be on a separate support board. A CPU board suitable for use with the present invention is Model SYS68K/CPU-29 from Force Computers, Inc. of Los Gatos, Calif.

CPU board 360 is connected by cable 342 to a terminal 362, which includes a keyboard 364. Terminal 362 allows the user to control operation of the apparatus by interacting with CPU board 360. A terminal used with the computer subsystem of the third embodiment of the present invention is the same as that used with the first two embodiments. CPU board 360 is connected to the rest of the computer subsystem via a VME bus 366. VME bus 366 transmits the control and data signals generated by CPU board 360 to other boards in computer subsystem 314. VME bus 366 is connected to beam position indicating assembly 340, light sensing assembly 344, belt position indicating assembly 360 and separation control assembly 370 as shown in FIG. 18. Separation control assembly 370 controls subsystem for separating contaminated particles which is shown at 380 in FIGS. 15 and 16.

A control and processor board 372 is connected to CPU board 360 via VME bus 366. Control and processor board 372 is also connected by cable 342 to photodetector assembly 344 for receiving, amplifying and filtering the signal generated by photodetector assembly 344.

The computer subsystem of the third embodiment of the present invention is substantially the same as that of the first two embodiments. However, control and processor board 372 as shown in FIG. 18 does not generate the BUF PMT, HSYNC, VSYNC and PXL CLK signals as shown in FIG. 5. However, it is noted that the apparatus of the third embodiment of the present invention does include separation control circuit 370, which is identical to separation control circuit 52 of the first embodiment as shown in FIGS. 4 and 5. Belt position indicating assembly 360 generates a belt position signal which is transmitted via cable 342 to VME bus 366 and then to CPU board 360. The CPU board uses the belt position signal to generate a control signal to the separation control circuit to activate separation subsystem 380 when the contaminant arrives. Since the particles are stationary with respect to the belt, the position of the contaminants is thus more precisely known, and a smaller quantity of particles is removed with the contaminant. The rest of computer subsystem 314 of the third embodiment is substantially the same as that described with reference to FIGS. 6–10 of the first embodiment of the present invention. The operation of the apparatus of the third embodiment is substantially the same as that described above for the first and second embodiments, except that, in addition to the differences noted above, the particles are moved through the integrating chamber by the oscillation of the belt, respectively, rather than by the oscillation of the integrating chamber as in the first embodiment, or the oscillation of the trough as in the second embodiment.

Figure 19:
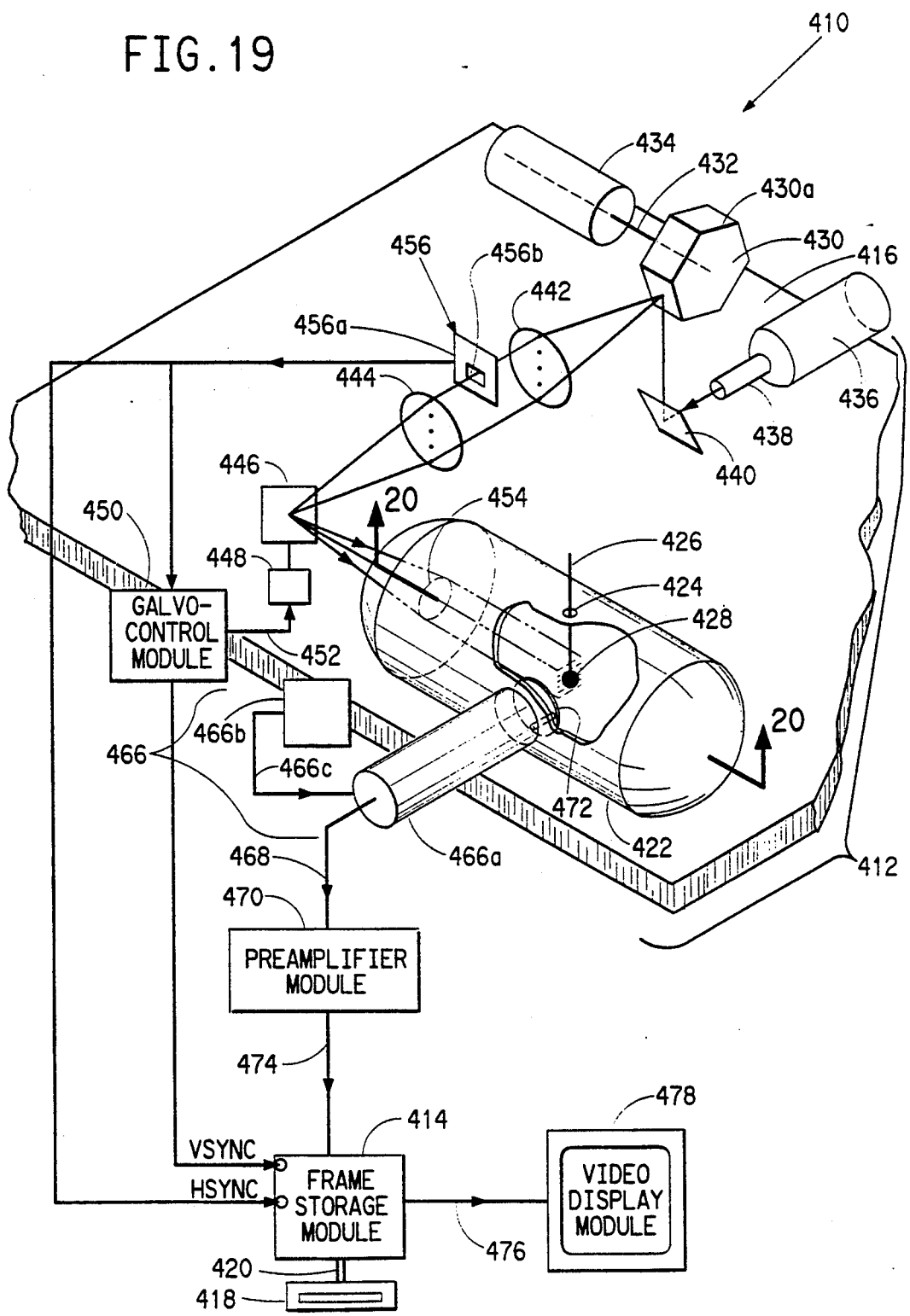
FIG. 19 is an isometric, schematic view of an apparatus for optically detecting contamination in particles of low optical-loss material with the integrating chamber partially cut away according to a fourth embodiment of the present invention.

A fourth embodiment of the present invention is shown and described with respect to FIGS. 19 and 20. An apparatus for optically detecting light-absorbing contamination in at least one particle of low optical-loss material according to the fourth embodiment of the present invention is shown generally at 410 in FIG. 19. Apparatus 410 comprises an optical subsystem 412 and a frame storage module 414. Optical subsystem 412 optically detects light-absorbing contamination in the particles and is mounted on an optical table 416 as shown in FIG. 19. Frame storage module 414 digitizes, stores and displays the optical image of the particles. Frame storage module includes a control panel 418 which is connected by a coaxial cable 420 to module 414. Control panel 418 allows the operator to control the operation of module 414. The frame storage module used with the present invention is a commercially available piece of equipment. A frame storage module suitable for use with the present invention is an image processor, sold under the trademark "CRYSTAL" by Quantex, Ltd. of Palo Alto, Calif.

The apparatus of the present invention also comprises an optical integrating chamber for containing the at least one particle. As shown in FIG. 19, apparatus 410 comprises an integrating chamber 422 which has a plurality of interior walls. The integrating chamber as shown in FIG. 19 is generally cylindrical in shape with hemispherical ends. However, the configuration of the integrating chamber of the fourth embodiment of the present invention may be modified without departing from the scope or spirit of the invention. For instance, the integrating chamber may be configured as an elongated, rectangular box. Integrating chamber 422 may be made of any suitable material, such as metal, (e.g., stainless steel) or plastic (e.g., polyvinyl chloride). The interior walls of the integrating chamber are coated with a nearly lambertian, diffusely reflective, light-scattering material. A paint containing barium sulfate, such as that used with the second and third embodiments, is suitable for this purpose. As shown in FIGS. 19 and 20, integrating chamber 422 is formed with an aperture 424 for allowing a rod 426 to be suspended therein. A particle 428 of low optical-loss material is suspended on the end of rod 426.

The apparatus of the present invention also comprises a laser 436 for emitting a laser beam to illuminate the at least one particle as shown in FIG. 19. The light from the laser beam is either transmitted through or reflected from the particle of low optical-loss material. The laser used in the present invention is a commercially available, off-the-shelf item, such as that used in the first three embodiments. However, other types of lasers may be used with the apparatus of the fourth embodiment of the present invention without departing from the scope or spirit of the present invention. Laser 436 preferably includes a telescopic lens assembly 438, which comprises a collimating lens and a beam expander, for collimating the laser beam. A suitable telescopic lens assembly for use with the fourth embodiment of the present invention, such as 3X beam expander, Model T81-3X from Tropel, Inc. of Rochester, N.Y., is used to expand and collimate the laser beam to a diameter of about three millimeters.

The apparatus in accordance with the fourth embodiment of the present invention further comprises a scanning assembly mounted in optical alignment with the laser for reflecting the laser beam and for causing the laser beam to scan the particles in the optical integrating chamber. In the fourth embodiment, the scanning assembly includes a rotating mirror 430 mounted adjacent integrating chamber 422 as shown in FIG. 19. Rotating mirror 430 has at least one reflective face 430a disposed about the circumference thereof and an axis of rotation generally perpendicular to the reflective face. Mirror 430 is supported on a shaft 432 and is rotatable by a motor 434 as shown in FIG. 19. Laser 436 is mounted on optical table 416 in the plane of rotation of rotating mirror 430 such that the laser beam reflects from reflective face 430a of rotating mirror 430 and scans in a fan scan. To reduce space requirements for the apparatus, the expanded beam from laser 436 is first reflected 90 upwardly from a beam-folding mirror 440 as shown in FIG. 19 to one of the reflective faces of the rotating mirror. The laser beam is thus reflected from reflective faces 430a in a fan scan in the vertical direction. A scanning assembly suitable for use with the fourth embodiment of the present invention is Model 18875H-23ND-2-100, which is commercially available from Lincoln Laser Company of Phoenix, Ariz. Alternatively, in the fourth embodiment of the present invention, the scanning assembly could be a galvanometer driven rotating mirror, a resonant torsional scanner, a holographic scanner or an accousto-optic deflector.

The apparatus in accordance with the present invention comprises an optical assembly mounted in optical alignment with the laser for converting the fan scan into a raster fan scan. The optical assembly comprises a relay lens assembly and a galvanometer assembly. The relay lens assembly comprises a first biconvex lens 442 for converting the fan scan into a telecentric scan and a second biconvex lens 444 for converting the telecentric scan into a converging fan scan. The galvanometer assembly comprises a galvo-mirror 446 for converting the converging fan scan into a diverging raster scan, a galvanometer 448 for causing the galvo-mirror to move back and forth and a galvo-control module 450 for converting the converging fan scan into a diverging raster scan. The operation of the galvocontrol module is described in U.S. Pat. No. 4,972,258, which is incorporated herein by reference. First biconvex lens 442 converts the collimated fan scan into a telecentric scan with the laser beam focused on a line midway between first and second biconvex lenses 442 and 444, respectively. Second biconvex lens 444 recollimates the laser beam and converts the incoming telecentric scan into a converging fan scan so that it is directed to a stationary spot, which is located on galvo-mirror 446, with the vertical angle of incidence varying as the beam scans. The stationary spot is located on galvo-mirror 446. The center of the laser beam intersects the vertical axis of galvanometer 448 at the vertical center of galvo-mirror 446. Galvanometer 448 causes galvomirror 446, which typically has rectangular faces, to rotate back and forth about a vertical axis coincident with the front face of the mirror. Galvanometer 448 includes a rotationally oscillating shaft, and the rotary back and forth movement of the galvanometer shaft causes galvo-mirror 446 to reflect the beam in a horizontal direction at an angle such that when combined with the motion of the laser beam incident on galvo-mirror 446 in the vertical direction created by rotating mirror 430, the collimated laser beam moves in a diverging raster fan scan. The raster scanning laser beam then enters integrating chamber 422. The galvanometer operates in response to electrical control signals carried over a cable 452 from galvanometer control module 450. A galvanometer suitable for use with the fourth embodiment of the present invention is commercially available as part number G120D from General Scanning Corporation of Watertown, Mass. A suitable galvo-mirror is five millimeters high by five millimeters wide by one millimeter thick, where the five millimeter-by-five millimeter faces are positioned in vertical planes. A galvo-mirror suitable for use with the fourth embodiment of the present invention can be obtained from Spectro-Film Company of Winchester, Mass.

The apparatus in accordance with the fourth embodiment of the present invention further comprises a focusing assembly mounted in optical alignment with the laser for focusing the scanning laser beam onto the particle in the chamber. The focusing assembly operates in conjunction with the scanning assembly so that light from the laser beam is reflected from the particle and is repeatedly scattered onto the interior walls of the integrating chamber. The focusing assembly comprises a scan lens 454 as shown in FIGS. 19 and 20 mounted between integrating chamber 422 and galvanometer 448. The scan lens converts the diverging raster scan into a telecentric raster scan. Scan lens 454 is disposed in an opening in one end of integrating chamber 422. The scan lens causes the beam to focus to a small spot inside integrating chamber 422 at a plane in which particle 428 lies. The plane is located one focal length from the lens. Integrating chamber 422 is positioned such that the intersection point of the beam with galvo-mirror 446 is one focal length of the scan lens from the scan lens. With the components of optical subsystem 412 so positioned, the diverging raster fan scan from the scanning assembly is converted to a telecentric raster scan after the beam passes through the scan lens.

The apparatus in accordance with the fourth embodiment of the present invention further comprises a laser beam position indicating assembly mounted in fixed relationship to the scanning assembly for detecting when the scanning laser beam reaches a predetermined point and for generating a scan detection signal in response thereto. Preferably, the laser beam position indicating assembly comprises a photodetector assembly 456. As shown in FIG. 19, photodetector assembly 456 is mounted adjacent integrating chamber 422 between first biconvex lens 442 and second biconvex lens 444. In this context, adjacent may mean either in, on or near. Photodetector assembly 456 includes a photodetector 456a and a scan detection circuit 456b. The details of the scan detection circuit are the same as those described above with respect to the first embodiment in FIG. 3. The photodetector of photodetector assembly 456 of the fourth embodiment is the same split photodiode as described in the first embodiment. Photodetector assembly 456 is mounted in a fixed relationship to the rotating mirror for detecting when the scanning laser beam from first biconvex lens 442 reaches a predetermined point near the end of the scan of the laser beam as it crosses photodetector 456a and for generating a scan detection signal in response thereto. Alternatively, the laser beam position indicating assembly comprises a magnetic detector for detecting the angular position of the scanning assembly.

The apparatus of the present invention further comprises a light sensing assembly for generating an intensity signal indicative of the intensity of the repeatedly scattered light, wherein a decrease in the intensity of the repeatedly scattered light is a function of the presence of light-absorbing contamination in the material. The light sensing assembly comprises a photodetector assembly 466 as shown in FIGS. 19 and 20 mounted adjacent integrating chamber 422. In this context, adjacent means in, on or near. Integrating chamber 422 is constructed with an opening for photodetector assembly 466 to extend therethrough. In the present invention, the area of the openings in the integrating chamber, including the opening for photodetector assembly 466 and the opening for rod 426, must be kept to a minimum for the integrating chamber to function in an optically efficient manner. Photodetector assembly 466 continuously senses variations in the intensity of light repeatedly scattered from the particle to detect contamination in the material. The photodetector assembly of the light sensing assembly typically includes a photomultiplier tube 466a and a high voltage power supply 466b for the photomultiplier tube. The gain of photodetector assembly 466 may be controlled by manually controlling the high voltage of high voltage power supply 466b. A suitable photomultiplier tube for use as the photodetector assembly of the light sensing assembly of the fourth embodiment of the present invention is Model 8654 from Burle Industries of Lancaster, Pa. A high voltage power supply suitable for use with the fourth embodiment of the present invention is Model PMT-10C/N from Bertan Associates, Inc. of Hicksville, N.Y. Although a photomultiplier tube is used with the fourth embodiment of the present invention, alternatively, the light sensing assembly may comprise another type of photodetector, such as a photodiode, or a vacuum photodiode. The apparatus of the fourth embodiment of the present invention operates according to the same optical principles as described above with respect to the first three embodiments, so that the intensity generated by photodetector assembly 466 is indicative of the intensity of the light repeatedly scattered from the interior walls of the integrating chamber.

The apparatus according to the fourth embodiment of the present invention further includes a signal processing assembly connected to the photodetector assembly of the light sensing assembly for amplifying and filtering the intensity signal. The signal processing assembly includes a preamplifier module 470. The intensity signal generated by photodetector assembly 466 is transmitted via a cable 468, which is preferably a coaxial shielded cable, to preamplifier module 470. Preamplifier module 470 amplifies the intensity signal generated by photodetector assembly 466 and converts it into a voltage intensity signal, which is transmitted to frame storage control module 414. The scan detection signal generated by the scan detection circuit of photodetector assembly 456 of the laser beam position indicating assembly is also transmitted to the input jack in frame storage control module 414 for the HSYNC signal, and causes frame storage control module 414 to digitize the voltage intensity signal generated by the photodetector assembly 466.

The apparatus in accordance with the fourth embodiment of the present invention further includes a video display section connected to the signal processing assembly for displaying the amplified and filtered signal. A video display module 478 is shown in FIG. 18. The intensity signal generated by photodetector assembly 466 is sent from frame storage module 414 via a cable 476 to video display module 478. Video display module 478 displays contaminated particles inside the integrating chamber. Frame storage module 414 has the capability of receiving the video signal from preamplifier module 470, sampling the video signal at a predetermined sample rate, converting the samples to digital values using an analog-to-digital converter and storing the digital values. The VSYNC signal generated by galvanometer control module 450 and the scan detection signal are used by video display module 478 to synchronize the stored digital values and thus create an image representing the optical absorption variations of the particle being inspected.

The apparatus of the present invention further comprises a baffle 472 mounted inside the integrating to ensure that only repeatedly scattered light is incident on the photodetector assembly of the light sensing assembly. Baffle 472 is mounted inside integrating chamber 422 in front of and spaced from the opening in which photodetector assembly 466 is provided as shown in FIGS. 19 and 20. The surfaces of the baffle are coated with a nearly lambertian, diffusely reflective, light-scattering material, such as the paint containing barium sulfate which is used to coat the interior walls of the integrating chamber. Baffle 472 ensures that only light which has been repeatedly scattered can reach photodetector assembly 466 as described above with respect to the first three embodiments.

The operation of the fourth embodiment of the present invention will now be described with respect to FIGS. 19 and 20. In operation, motor 434 is turned on to start the rotation of mirror 430, and laser 436 is turned on and begins to emit a laser beam. Both rotating mirror 430 and laser 436 operate continuously. The laser beam emitted by laser 436 is reflected from beam folding mirror 440 to a reflective face of rotating mirror 430. The laser beam scans in a fan scan as it reflects from reflective face 430a of rotating mirror 430 to first biconvex lens 442 and is telecentric as it scans photodetector 456 of the laser beam position indicating assembly. The telecentric scanning laser beam then passes through second biconvex lens 444 and is converted to a converging fan scan, and converges onto a spot on galvo-mirror 446, which is rotated back and forth under control of galvo-control module 450. The beam to fan scan to scanning laser beam to converging fan scan is thus converted into a raster scan and diverges from galvo-mirror 446 until it reaches scan lens 454. Scan lens 454 converts the diverging raster scan into a telecentric raster scan.

As soon as both motor 434 and laser 436 begin to operate, photodetector assembly 456 begins to generate a plurality of repetitive scan detection signals. The scan detection signals are continuously transmitted to galvo-control module 450, which moves galvo-mirror 446 in synchronism with rotating mirror 430. Galvo-control module 450 in turn sends the VSYNC signal to frame storage module 414. The scan detection signals are also sent to frame storage module 414 as the HSYNC signal to synchronize the operation of the module with the rotation of mirror 430.

A particle of material to be inspected is held at the focal plane of the telecentric raster scan. The repetitive, continuous scan detection signal generates the HSYNC signal. As the laser beam sweeps across the particle, the intensity of the light reflected from and passing through the particle is sensed by photodetector assembly 466. Photodetector assembly 466 converts the sensed light to an intensity signal indicative of the intensity of the repeatedly scattered light from the interior walls of the integrating chamber. The light absorption of the contamination causes a decrease in the intensity of the repeatedly scattered light within the integrating chamber. The decrease in the intensity of the repeatedly scattered light is thus a function of the presence of light-absorbing contamination in the material.

Additional advantages and modifications will readily occur to those skilled in the art. The invention in its broader aspects is, therefore, not limited to the specific details and representative apparatus shown and described. Accordingly, departures may be made from such details without departing from the spirit or scope of the general inventive concept as defined by the appended claims and their equivalents.

We claim:

1. An apparatus for optically detecting light-absorbing contamination in at least one particle of low optical-loss material, comprising:
   (a) an optical integrating chamber for containing a particle of low-optical loss material, the optical integrating chamber having a plurality of interior walls;

(b) a laser for emitting a laser beam to illuminate the particle;

(c) a scanning assembly mounted in optical alignment with the laser for reflecting the laser beam and for causing the laser beam to scan the particle in the optical integrating chamber;

(d) a focusing assembly mounted in optical alignment with the laser for focusing the scanning laser beam onto the particle in the chamber, the focusing assembly operating in conjunction with the scanning assembly so that light from the laser beam is reflected from the particle and is repeatedly scattered onto the interior walls of the integrating chamber; and (e) a light sensing assembly for generating an intensity signal indicative of the intensity of the repeatedly scattered light, wherein a decrease in the intensity of the repeatedly scattered light is a function of the presence of light-absorbing contamination in the material.

2. The apparatus as claimed in claim 1, wherein the integrating chamber is lined with a diffusely reflective material.

3. The apparatus as claimed in claim 1, wherein the integrating chamber comprises an upper portion and a lower portion.

4. The apparatus as claimed in claim 3, wherein the upper portion of the integrating chamber comprises a stationary cover.

5. The apparatus as claimed in claim 3, wherein the lower portion includes a substantially planar surface for containing and transporting the particles.

6. The apparatus as claimed in claim 5, wherein each of the upper portion and the lower portion includes an upper peripheral edge and a lower peripheral edge and an opening is formed at each longitudinal end of the upper and lower portions by the planar surface of the lower portion and the lower peripheral edge of the upper portion.

7. The apparatus as claimed in claim 5, wherein the integrating chamber is substantially elongated and has a longitudinal axis and the planar surface has a longitudinal axis, the longitudinal axis of the integrating chamber and the longitudinal axis of the planar surface being substantially parallel.

8. The apparatus as claimed in claim 7, wherein the lower portion comprises a trough of an oscillating feeder assembly.

9. The apparatus as claimed in claim 8, further including a motor for driving the trough in an oscillatory manner along the longitudinal axis of the integrating chamber so that the particles are transported through the chamber along the planar surface of the lower portion.

10. The apparatus as claimed in claim 1, wherein the laser includes a telescopic lens assembly for collimating the beam.

11. The apparatus as claimed in claim 1, wherein the scanning assembly includes a rotating mirror mounted adjacent the integrating chamber, the mirror having at least one reflective face.

12. The apparatus as claimed in claim 11, wherein the laser is mounted in the plane of rotation of the rotating mirror such that the laser beam reflects from the reflective face of the rotating mirror and scans in a fan scan.

13. The apparatus as claimed in claim 12, wherein the focusing assembly comprises a scan lens mounted between the integrating chamber and the rotating mirror and converts the fan scan into a telecentric scan.

14. The apparatus as claimed in claim 1, further including a laser beam position indicating assembly mounted in a fixed relationship to the scanning assembly for detecting when the scanning laser beam reaches a predetermined point and for generating a scan detection signal in response thereto.

15. The apparatus as claimed in claim 14, wherein the laser beam position indicating assembly comprises a photodetector assembly and a scan detection circuit.

16. The apparatus as claimed in claim 1, wherein the light sensing assembly comprises a photodetector assembly mounted adjacent the integrating chamber for receiving the light repeatedly scattered in the chamber.

17. The apparatus as claimed in claim 16, further including a baffle mounted inside the integrating chamber to ensure that only repeatedly scattered light is incident on the photodetector assembly.

18. The apparatus as claimed in claim 16, further including a signal processing assembly connected to the photodetector assembly of the light sensing assembly for amplifying and filtering the intensity signal.

19. The apparatus as claimed in claim 18, further including a video display section connected to the signal processing assembly for displaying the amplified and filtered signal.

20. The apparatus as claimed in claim 19, further including an automatic gain control section connected to the signal processing assembly for generating a control signal in response to changes in at least one of: the amount of optical power entering the chamber from the laser, the scattering efficiency of the integrating chamber and the sensitivity of the photodetector assembly.

21. The apparatus as claimed in claim 20, further including a digital-to-analog converter connected to the automatic gain control section for generating a plurality of DC reference voltages.

22. The apparatus as claimed in claim 21, further including a thresholding section comprising a plurality of comparators for comparing the plurality of DC reference voltages to the amplified and filtered signal.

23. The apparatus as claimed in claim 3, wherein the integrating chamber is substantially spherical in shape.

24. The apparatus as claimed in claim 3, further including a transparent trough for containing and transporting the particles disposed between the upper portion and the lower portion of the integrating chamber, the trough having a longitudinal axis and being adapted for oscillation therealong.

25. The apparatus as claimed in claim 24, wherein the lower portion of the integrating chamber has a planar surface and the upper portion of the integrating chamber has a lower peripheral edge, and further wherein an opening is formed at each longitudinal end of the upper and lower portions by the planar surface of the lower portion and the lower peripheral edge of the upper portion.

26. The apparatus as claimed in claim 25, wherein the trough includes a damper disposed at one longitudinal end thereof to reduce the vertical vibration of the trough and to keep the particles from bouncing vertically.

27. The apparatus as claimed in claim 25, further including a flow-regulating gate for regulating the flow of the particles at the entrance to the trough.

28. The apparatus as claimed in claim 24, further including a vibratory feeder assembly for feeding particles to the trough at a controlled rate.

29. The apparatus as claimed in claim 3, further including a transparent belt for holding and transporting the particles disposed between the upper portion and the lower portion of the integrating chamber, the belt having a longitudinal axis and being adapted for movement therealong.

30. The apparatus as claimed in claim 29, further including a screw-feed system for feeding the particles onto the belt at a controlled rate.

31. The apparatus as claimed in claim 29, further including a flow-regulating gate for regulating the flow of the particles at the entrance to the belt.

32. The apparatus as claimed in claim 12, wherein the focusing assembly comprises an optical assembly mounted in optical alignment with the laser for converting the fan scan into a diverging raster scan.

33. The apparatus as claimed in claim 32, wherein the optical assembly comprises a relay lens assembly and a galvanometer assembly.

34. The apparatus as claimed in claim 33, wherein the relay lens assembly comprises a first biconvex lens for converting the fan scan into a telecentric scan and a second biconvex lens for coverting the telecentric scan into a converging fan scan.

35. The apparatus as claimed in claim 34, further including a laser beam position indicating assembly including a photodetector assembly and a scan detection circuit, wherein the photodetector assembly is positioned between the first and second biconvex lenses.

36. The apparatus as claimed in claim 34, wherein the galvanometer assembly comprises a galvo-mirror for converting the converging fan scan into a diverging raster scan, a galvanometer for causing the galvo-mirror to move back and forth and a galvo-control module for controlling the operation of the galvanometer.

37. The apparatus as claimed in claim 36, wherein the focusing assembly includes a scan lens mounted between the integrating chamber and the galvanometer for converting the diverging raster scan into a telecentric raster scan.

* * * * *